US008114894B2

(12) United States Patent
Ghosh et al.

(10) Patent No.: US 8,114,894 B2
(45) Date of Patent: Feb. 14, 2012

(54) BICYCLIC COMPOUNDS AND METHODS OF MAKING AND USING SAME

(75) Inventors: Shomir Ghosh, Brookline, MA (US); Gali Golan, Kfar Vitkin (IL); Boaz Inbal, Kfar Shmuel (IL); Vincent Jacques, Somerville, MA (US); Mercedes Lobera, Bolton, MA (US)

(73) Assignee: Nanotherapeutics, Inc., Alachua, FL (US)

( * ) Notice: Subject to any disclaimer, the term of this patent is extended or adjusted under 35 U.S.C. 154(b) by 0 days.

(21) Appl. No.: 12/630,468

(22) Filed: Dec. 3, 2009

(65) Prior Publication Data
US 2010/0197723 A1 Aug. 5, 2010

Related U.S. Application Data

(60) Provisional application No. 61/119,538, filed on Dec. 3, 2008.

(51) Int. Cl.
*A61K 31/404* (2006.01)
*C07D 401/12* (2006.01)

(52) U.S. Cl. ........................................ 514/323; 546/201
(58) Field of Classification Search .................... 546/201
See application file for complete search history.

(56) References Cited

U.S. PATENT DOCUMENTS

| | | | |
|---|---|---|---|
| 3,069,412 A | 12/1962 | Roberts et al. |
| 3,658,807 A | 4/1972 | Schmidt et al. |
| 4,146,716 A | 3/1979 | Cox et al. |
| 4,316,020 A | 2/1982 | Reissenweber et al. |
| 5,155,155 A | 10/1992 | Jurlaro et al. |
| 5,219,864 A | 6/1993 | Suzuki et al. |
| 5,227,387 A | 7/1993 | Dreikorn et al. |
| 5,236,917 A | 8/1993 | Dunlap et al. |
| 5,371,074 A | 12/1994 | Dunlap et al. |
| 5,378,679 A | 1/1995 | Nuebling et al. |
| 5,571,815 A | 11/1996 | Schaper et al. |
| 5,591,751 A | 1/1997 | Fuljoka et al. |
| 5,593,943 A | 1/1997 | Nuebling et al. |
| 5,596,012 A | 1/1997 | Dunlap et al. |
| 5,650,422 A | 7/1997 | Dunlap et al. |
| 5,753,673 A | 5/1998 | Ohuchi et al. |
| 5,798,451 A | 8/1998 | von Deyn et al. |
| 5,874,432 A | 2/1999 | Dunlap et al. |
| 5,972,841 A | 10/1999 | von Deyn et al. |
| 6,103,903 A | 8/2000 | Cai et al. |
| 6,159,962 A | 12/2000 | Steiner et al. |
| 6,187,788 B1 | 2/2001 | Furuya et al. |
| 6,222,034 B1 | 4/2001 | Steiner et al. |
| 6,232,320 B1 | 5/2001 | Stewart et al. |
| 6,300,333 B1 | 10/2001 | Schaper et al. |
| 6,340,759 B1 | 1/2002 | Ueno et al. |
| 6,596,727 B1 | 7/2003 | Schaper et al. |
| 6,924,283 B2 | 8/2005 | Thorarensen |
| 7,030,240 B2 | 4/2006 | Dhanoa et al. |
| 7,119,205 B2 | 10/2006 | Iyengar et al. |
| 7,153,858 B2 | 12/2006 | Dhanoa et al. |
| 7,407,966 B2 | 8/2008 | Dhanoa et al. |
| 7,488,736 B2 | 2/2009 | Dhanoa et al. |
| 7,576,211 B2 | 8/2009 | Dhanoa et al. |
| 7,598,265 B2 | 10/2009 | Dhanoa et al. |
| 2002/0028782 A1 | 3/2002 | Castelhano et al. |
| 2004/0138238 A1 | 7/2004 | Dhanoa et al. |
| 2005/0049243 A1 | 3/2005 | Ballard et al. |
| 2005/0065176 A1 | 3/2005 | Field et al. |
| 2005/0137142 A1 | 6/2005 | Schulz et al. |
| 2005/0222175 A1 | 10/2005 | Dhanoa et al. |
| 2005/0222176 A1 | 10/2005 | Dhanoa et al. |
| 2005/0256153 A1 | 11/2005 | Dhanoa et al. |
| 2006/0079547 A1 | 4/2006 | Dhanoa et al. |
| 2006/0084805 A1 | 4/2006 | Dhanoa et al. |
| 2006/0084806 A1 | 4/2006 | Sridharan et al. |
| 2006/0205737 A1 | 9/2006 | Becker et al. |
| 2006/0234998 A1 | 10/2006 | Dhanoa et al. |
| 2007/0004742 A1 | 1/2007 | Dhanoa et al. |
| 2007/0173487 A1 | 7/2007 | Saha et al. |

FOREIGN PATENT DOCUMENTS

| | | |
|---|---|---|
| CA | 2038521 | 9/1991 |
| EP | 0447891 | 9/1991 |
| EP | 0503844 A | 9/1992 |
| EP | 0505058 A | 9/1992 |
| EP | 0710662 A1 | 5/1996 |
| EP | 1018513 | 7/2000 |
| EP | 1229025 | 8/2002 |
| EP | 1325921 | 7/2003 |
| GB | 2295387 | 5/1996 |
| JP | 11 130777 A | 5/1999 |
| WO | WO-94/12176 | 6/1994 |
| WO | WO-94/22871 | 10/1994 |
| WO | WO-00/64441 A | 11/2000 |
| WO | WO 00/71535 A1 | 11/2000 |
| WO | WO-01/14333 | 3/2001 |
| WO | WO-01/25218 | 4/2001 |
| WO | WO-02/102797 | 12/2002 |
| WO | WO-2004/014850 | 2/2004 |
| WO | WO-2004/017950 | 3/2004 |

(Continued)

OTHER PUBLICATIONS

Chodnekar, et al. Document No. 76:94939, retrieved from CAPLUS (1972).* Chodnekar, M.S. et al., "β-Adrenergic Blocking Agents. 11. Heterocyclic Analogs of Pronethalol [2-Isopropylamino-1-(2-naphthyl)ethanol]", *Journal of Medicinal Chemistry*, vol. 15, No. 1, 1971, pp. 49-57.
Da Settimo, A. et al., "N-Phenylindol-3-ylglyoxylohydrazide Derivatives: Synthesis, Structure-Activity Relationships, Molecular Modeling Studies, and Pharmacological Action on Brain Benzodiazepine Receptors", *Journal of Medicinal Chemistry*, vol. 41, No. 20, 1998, pp. 3821-3830.
Van Hooft, J.A. et al., "RS-056812-198: partial agonist on native and antagonist on cloned 5-HT$_3$ receptors", *European Journal of Pharmacology*, vol. 322, 1997, pp. 229-233.
Abenhaim et al. N. Engl. J. Med., 335(9):609-616 (1996).
Barker et al., Journal of Chemical Research, Synopses, 1985 (7) 214-15.
Bonhaus, D.W., et al., British J. Pharmac., 1999 (127) 1075-1082.
Brea et al., J. Med. Chem., 45:54-71 (2002).

(Continued)

*Primary Examiner* — Shawquia Young
(74) *Attorney, Agent, or Firm* — Finnegan, Henderson, Farabow, Garrett & Dunner, LLP

(57) ABSTRACT

Disclosed herein are compounds that may be modulators of 5-HT receptors, and methods of making and using same.

4 Claims, No Drawings

FOREIGN PATENT DOCUMENTS

| | | |
|---|---|---|
| WO | WO-2004/030629 | 4/2004 |
| WO | WO-2004/034963 | 4/2004 |
| WO | WO-2004/089312 | 10/2004 |
| WO | WO-2005/121151 | 12/2005 |
| WO | WO 2006/015867 A1 | 2/2006 |
| WO | WO-2006/041985 | 4/2006 |
| WO | WO-2007/058805 | 5/2007 |
| WO | WO-2008/002539 | 1/2008 |
| WO | WO-2008/045558 | 4/2008 |
| WO | WO-2008/060632 | 5/2008 |

OTHER PUBLICATIONS

Buchheit et al. J. Med. Chem., 38(13):2326-2330 (1995).
Buchheit et al. J. Med. Chem., 38(13):2331-2338 (1995).
Buchstaller, H.P. et al., "Thieno[2,3-b]pyridinones as Antagonists on the Glycine Site of the N-methyl-D-aspartate Receptor-Binding Studies, Molecular Modelling and Structure-Activity Relationships", Scientia Pharmazeutica, 68, 3-14 (2000).
Coppola et al., Journal of Organic Chemistry, 1976 (41) 825-831.
Database Caplus on STN, Accession No. 1999:783937, Castelhano et al., WO 99/62518 A1, Cadue Pharmaceuticals Corp. Dec. 9, 1999.
Database Caplus on STN, Accession No. 2000:806616 Horvath et al., Neurogen Corporation, 6,147,085, Nov. 14, 2000.
Doggrell, Sheila A., Expert Opin. Investig. Drugs, 2003 (12) 805-823.
Farber et al., N. Engl. J. Med., 351 (16):1655-1665 (2004).
Fishman, Chest, 114(3):242S-247S (1998).
Fitzgerald et al. Mol. Pharmacol., 57:75-81 (2000).
Gribble, Gordon W., Sodium Borohydride in Carboxylic Acid Media: A Phenomenal Reduction System, Chemical Society Reviews, 1998 (27) 395-40.
Hutchins, R.O. et al., J. Org. Chem., 1977 (42) 82-91.
Hwang et al., Arch. of Pharm. Res., 2001, 24(4), 270-275.
International Search Report for PCT/US2003/23539 mailed Jul. 23, 2004.
International Search Report for PCT/US2004/09944 mailed Mar. 1, 2005.
International Search Report for PCT/US2005/035935 mailed May 12, 2006.
International Search Report for PCT/US2005/034862 mailed Jan. 24, 2006.
International Search Report for PCT/US2005/17121 mailed Apr. 4, 2006.
International Search Report for PCT/US2006/043140 mailed Aug. 16, 2007.
Jerry March in Advanced Organic Chemistry, 4$^{th}$ Ed., 1992, by John Wiley & Sons: New York, pp. 378-383.
Kaumann, A.J., Naunyn-Schmiedeberg's Arch. Pharmacol., 342:619-622 (1990).
Kennett et al., Neuropharmacol., 36(2):233-239 (1997).
Kursar et al. Mol. Pharmacol., 46(2):227-234 (1994).
Kuryshev et al., J. Pharmacol. Exp. Ther., 295(2):614-620 (2000).
Lamirault L. et al., "Combined Treatment With Galanthaminium Bromide, a New Cholinesterase Inhibitor, and RS 67333, a Partial Agonist of 5-HT4 Receptors, Enhances Place and Object Recognition in Young Adult and Old Rats," Progress in Neuro-Psychopharmacology & Biological Psychiatry, Oxford, Great Britain, vol. 27, No. 1, Feb. 2003, pp. 185-195, XP008043794 ISSN: 0278-5846.
Launay et al., Nat. Med., 8(10):1129-1135 (2002).
MacLean, Margaret R., Trends Pharmacol. Sci., 20(12):490-495 (1999).
Manivert et al., J. Biol. Chem., 277(19):17170:17178 (2002).
Marcos et al., Circ. Res., 94:1263-1270 (2004).
Moser, Paul C. et al., "SL65.0155, a novel 5-hydroxytryptamine4 receptor partial agonist with potent cognition-enhancing properties," Journal of Pharmacology and Experimental Therapeutics (2002), 302(2), 731-741 CODEN: JPETAB; ISSN: 0022-3565, 2002, XP007902745.
Nauser et al., Am. Fam. Physician, 63(9):1789-1798 (2001).
Nebigil et al., Proc. Natl. Acad. Sci., U.S.A., 97(6):2591-2596 (2000).
Poissonnet et al., Mini-Rev. Med. Chem., 4(3):325-330 (2004).
Recanatini, M. et al., "Acetylcholinesterase Inhibitors in the Context of Therapeutic Strategies to Combat Alzheimer's Disease," Expert Opinion on Therapeutic Patents, Ashley Publications, Great Britain, vol. 12, No. 12, 2002, pp. 1853-1865, XP008043793 ISSN: 1354-3776.
Rich et al., CHEST, 117(3): 870-874 (2000).
Roth, B.L., et al., Expert Opin. Ther. Targets, 2001, (5) 685-695.
Rothman et al., Circulation, 102:2836-2841 (2000).
Science IP Search, Apr. 30, 2004.
Science IP Search, May 11, 2004.
Setola et al., Mol. Pharmacol., 63(6):1223-1229 (2003).
Stachel, Hans-Dietrich, et al., "Derivatives of Oxalyldimalonic Acid," 1995.
Suzuki, M., "Synthesis and Evaluation of Novel 2-Oxo-1,2-dihydro-3-Quinolinecarboxamide Derivatives as Potent and Selective Sarotonin 5-HT4 Receptor Agonists," Chem Pharm. Full., 49(1) 28-39, 2001.
Takashi et al., Bioorganic & Medicinal Chemistry Letters, 2002 (12) 2427-2430.
Teoh et al., "Hypoxia Enhances 5-HT$_{2B}$ Receptor Response and Expression the Rat Pulmonary Artery", Abstract only, International Conference of the American Thoracic Society, San Diego (May 24, 2005).
Ullmer et al., FEBS Lett., 370(3):215-221 (1995).
Ullmer et al. Br. J. Pharmacol., 117(6):1081-1088 (1996).
Witchel et al., FEBS Lett., 512(1-3):59-66 (2002).
Witchel et al., J. Clin. Psychopharmacol., 23(1):58-77 (2003).
Yamada et al., Eur. J. Pharmacol., 406(1):153-157 (2000).
U.S. Appl. No. 11/595,806, filed Nov. 9, 2006 (abandoned).
U.S. Appl. No. 12/570,510, filed Sep. 30, 2009.
Restriction Requirement dated May 18, 2007, for co-pending U.S. Appl. No. 10/955,434.
Response to Restriction Requirement dated Jun. 18, 2007, for co-pending U.S. Appl. No. 10/955,434.
Non-final Office Action dated Aug. 20, 2007, for co-pending U.S. Appl. No. 10/955,434.
Response to Non-final Office Action dated Dec. 18, 2007, for co-pending U.S. Appl. No. 10/955,434.
Non-final Office Action dated Apr. 1, 2008, for co-pending U.S. Appl. No. 10/955,434.
Response to Non-final Office Action dated Jul. 14, 2008, for co-pending U.S. Appl. No. 10/955,434.
Notice of Allowance dated Nov. 25, 2008, for co-pending U.S. Appl. No. 10/955,434.
Non-final Office Action dated Nov. 2, 2005, for co-pending U.S. Appl. No. 10/960,769.
Response to Non-final Office Action dated Dec. 5, 2005, for co-pending U.S. Appl. No. 10/960,769.
Notice of Allowance dated Dec. 16, 2005, for co-pending U.S. Appl. No. 10/960,769.
Non-final Office Action dated May 29, 2007, for co-pending U.S. Appl. No. 11/269,042.
Response to Non-final Office Action dated Nov. 23, 2007, for co-pending U.S. Appl. No. 11/269,042.
Response to Non-final Office Action dated Jan. 31, 2008, for co-pending U.S. Appl. No. 11/269,042.
Final Office Action dated Mar. 27, 2008, for co-pending U.S. Appl. No. 11/269,042.
Response to Final Office Action dated Jul. 17, 2008, for co-pending U.S. Appl. No. 11/269,042.
Notice of Allowance dated Nov. 4, 2008, for co-pending U.S. Appl. No. 11/269,042.
Supplemental Amendment dated Apr. 1, 2009, for co-pending U.S. Appl. No. 11/269,042.
Notice of Allowance dated Apr. 24, 2009, for co-pending U.S. Appl. No. 11/269,042.
Non-final Office Action dated Jul. 2, 2008, for co-pending U.S. Appl. No. 11/271,019.
Response to Non-final Office Action dated Oct. 28, 2008, for co-pending U.S. Appl. No. 11/271,019.
Response to Non-final Office Action dated Dec. 1, 2008, for co-pending U.S. Appl. No. 11/271,019.

Notice of Allowance dated May 22, 2009, for co-pending U.S. Appl. No. 11/271,019.
Non-final Office Action dated Jun. 21, 2010, for co-pending U.S. Appl. No. 12/343,818.
Response to Non-final Office Action dated Dec. 21, 2010, for co-pending U.S. Appl. No. 12/343,818.

Notice of Allowance dated Mar. 17, 2011, for co-pending U.S. Appl. No. 12/343,818.
Non-final Office Action dated Jun. 8, 2011, for co-pending U.S. Appl. No. 12/570,510.

* cited by examiner

BICYCLIC COMPOUNDS AND METHODS OF MAKING AND USING SAME

This application claims the benefit of U.S. Provisional Application No. 61/119,538, filed Dec. 3, 2008, which is incorporated herein by reference in its entirety.

The invention generally relates to the field of serotonin (5-hydroxytryptamine, or 5-HT) receptor modulators, e.g., agonists, partial agonists, inverse agonists, antagonists, and to new heterocyclic compounds, the synthesis and use of these compounds and their pharmaceutical compositions, e.g., in the treatment, modulation and/or prevention of physiological conditions associated with serotonin action, such as in treating Alzheimer's disease, Parkinson's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

The 5-HT$_4$ receptors represent a member of the family of receptors with seven transmembrane (7™) domains coupled to a G-protein which is positively coupled to adenylate cyclase. The 5-HT$_4$ receptors are expressed in a wide variety of tissues, including the human brain and the rodent brain, the human, dog, pig and rodent gastro-intestinal tract, and the pig and human heart. In the mammalian brain, the 5-HT$_4$ receptors contribute to dopamine secretion and regulate learning and long-term memory via the modification of acetylcholine release. In the peripheral tissues, the 5-HT$_4$ receptors have proven to regulate gastro-intestinal tract motility, intestinal electrolyte secretion, adrenal secretion of corticosteroids, bladder contraction and atrium contractility.

The 5-HT$_4$ receptors are involved in a wide variety of central and peripheral disorders, including cardiac arrhythmias and neurodegenerative disorders and more specifically Alzheimer's disease, Parkinson's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

5-HT receptor modulators e.g., agonists, partial agonists, inverse agonists and antagonists, and/or selective serotonin reuptake inhibitors (SSRIs) such as fluoxetine, paroxetine, fluvoxamine, sertraline, lorazepam, imipramine, citalopram, and nortriptyline, may be used for the treatment of the above conditions, as well as for vasodilation, angina, smooth muscle contraction, bronchoconstriction, and neuropathological disorders including Parkinson's disease and Alzheimer's disease. They also intervene in the regulation of the cerebral circulation and thus represent effective agents for controlling migraine. They are also suitable for the prophylaxis and control of the effects of occurrences of cerebral infarct (Apoplexia cerebri) such as stroke or cerebral ischemia. They are also suitable for the control of disorders of the intestinal tract which are characterized by disturbances of the serotoninergic system and also by disturbances of the carbohydrate metabolism. They are suitable for the treatment of gastrointestinal disorders including irritable bowel syndrome.

The development of 5-HT$_4$ receptor modulators, e.g., agonists, partial agonists, inverse agonists and antagonists, may have therapeutic applications in the central nervous system for treating neuropsychiatric disorders associated with a dysfunction of the central dopaminergic system, such as Parkinson's disease, or for treating amnesic deficiencies as presented in patients suffering from Alzheimer's disease. Such medicines might also be useful for treating peripheral disorders such as irritable bowel syndrome, gastroparesia, urinary incontinence and cardiac arrhythmias. Selective, high affinity, metabolically stable 5-HT$_4$ receptor modulators that possess good bioavailability, CNS penetration, and good pharmacokinetic properties, e.g., in vivo, are desirable.

This disclosure is generally directed to compounds which may be serotonin (5-hydroxytryptamine, or 5-HT) receptor modulators, and their use as, for example, medicinal agents. Also provided are pharmaceutical compositions comprising at least one disclosed compound, or pharmaceutically acceptable salt or N-oxide thereof, and a pharmaceutically acceptable carrier.

One embodiment provides compounds represented by formula I, and compositions comprising such compounds:

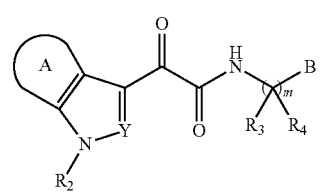

wherein Y is N or CH;

A is a monocyclic 5 or 6 membered aryl or hetoroaryl optionally substituted with one, two, three, or four substituents independently, for each occurrence, selected from the group consisting of halogen, hydroxyl, $C_1$-$C_6$ alkyl, $C_1$-$C_6$ haloalkyl, $C_3$-$C_6$ cycloalkyl, $C_1$-$C_6$ alkoxy, nitro, cyano, amino, sulfonyl, $C_1$-$C_6$ alkylsulfonyl, sulfamoyl, carbamoyl, carboxyl, N—($C_1$-$C_6$ alkyl)sulfamoyl, and N—($C_1$-$C_6$ alkyl)carbamoyl;

B is selected from formulae IA, IB, or IC;

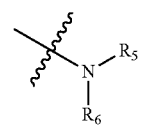

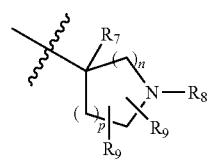

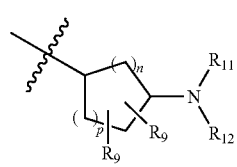

$R_2$ is selected from $C_1$-$C_6$ alkyl or $C_3$-$C_6$cycloalkyl, wherein $R_2$ may be optionally substituted with one, two, or three substituents selected, independently for each occurrence, from the group consisting of halogen, alkoxy, nitro, cyano, amino, and carboxyl;

$R_3$ and $R_4$ are each independently selected from the group consisting of hydrogen, $C_1$-$C_6$ alkyl, $C_1$-$C_6$alkoxy, aryl, $C_3$-$C_6$cycloalkyl, halogen, heteroaryl, heterocyclyl, and hydroxyl, wherein $R_3$ or $R_4$, if not hydrogen, may be optionally substituted by one, two, or three substituents represented by $R_{10}$, or $R_3$ and $R_4$ are taken together with the carbon atom to which they are attached to form a 5 to 6 membered heterocyclyl or $C_3$-$C_6$cycloalkyl optionally substituted by one, two, or three substituents each represented by $R_{10}$;

$R_5$ and $R_6$ are each independently selected from the group consisting of $C_1$-$C_6$alkyl, aryl, $C_3$-$C_6$ cycloalkyl, heteroaryl, heterocyclyl, and hydrogen, wherein $R_5$ or $R_6$, if not hydrogen, may be optionally substituted by one, two, or three substituents each represented by $R_{10}$, or $R_5$ and $R_6$ are taken together with the nitrogen atom to which they are attached to form a five or six membered heterocyclyl optionally substituted by one, two, or three substituents each independently represented by $R_{10}$;

$R_{11}$ and $R_{12}$ are each independently selected from the group consisting of $C_1$-$C_6$alkyl, aryl, $C_3$-$C_6$ cycloalkyl, heteroaryl, heterocyclyl, and hydrogen, wherein $R_{11}$ or $R_{12}$, if not hydrogen, may be optionally substituted by one, two, or three substituents each represented by $R_{10}$, or $R_{11}$ and $R_{12}$ are taken together with the nitrogen atom to which they are attached to form a heterocyclyl optionally substituted by one, two, or three substituents each independently represented by $R_{10}$;

$R_7$ is selected from the group consisting of $C_1$-$C_6$alkoxy, $C_1$-$C_6$alkyl, cyano, halogen, hydrogen, and hydroxyl;

$R_8$ is selected from hydrogen or alkyl optionally substituted by one, two, or three substituents selected from the group consisting of halogen, hydroxyl, $C_1$-$C_6$alkylsulfonyl, $C_1$-$C_6$alkoxy, N—$C_1$-$C_6$alkylamino, N,N-di $C_1$-$C_6$alkylamino, cyano, carboxyl, sulfonamido, and $C_1$-$C_6$alkylsulfonamido;

$R_9$ is, independently for each occurrence, selected from the group consisting of hydrogen, halogen, hydroxyl, nitro, cyano, amino, sulfonyl, $C_1$-$C_6$alkylsulfonyl, sulfamoyl, sulfonamido, $C_1$-$C_6$alkylsulfonamido, carbamoyl, carboxyl, N—$C_1$-$C_6$alkylsulfamoyl, N—$C_1$-$C_6$alkylcarbamoyl, alkyl, $C_3$-$C_6$cycloalkyl, $C_1$-$C_6$alkylthio, and $C_1$-$C_6$alkoxy, wherein the alkyl, cycloalkyl or alkoxy is optionally substituted by one, two, or three substituents selected from the group consisting of halogen, hydroxyl, carboxy, cyano, amido, nitro, and amino;

$R_{10}$ is selected from the group consisting of halogen, hydroxyl, nitro, cyano, amino, sulfonyl, $C_1$-$C_6$alkylsulfonyl, sulfamoyl, sulfonamido, $C_1$-$C_6$alkylsulfonamido, carbamoyl, carboxyl, N—$C_1$-$C_6$alkylsulfamoyl, N—$C_1$-$C_6$alkylcarbamoyl, $C_1$-$C_6$alkyl, $C_3$-$C_6$cycloalkyl, $C_1$-$C_6$ alkylthio, and $C_1$-$C_6$alkoxy, wherein the alkyl, cycloalkyl or alkoxy is optionally substituted by one, two, or three substituents selected from the group consisting of halogen, hydroxyl, carboxy, cyano, amido, nitro, and amino;

m is 0, 1, 2, 3, or 4;

n is 0, 1, or 2; and p is 0, 1 or 2;

or pharmaceutically acceptable salts or N-oxides thereof.

Another embodiment provides compounds represented by formula II, and compositions comprising such compounds:

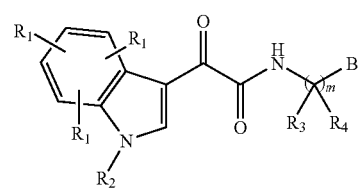

II wherein $R_1$ is independently, for each occurrence, selected from the group consisting of halogen, hydroxyl, $C_1$-$C_6$alkyl, $C_1$-$C_6$haloalkyl, $C_3$-$C_6$cycloalkyl, $C_1$-$C_6$alkoxy, nitro, cyano, amino, sulfonyl, $C_1$-$C_6$alkylsulfonyl, sulfamoyl, carbamoyl, carboxyl, N—$C_1$-$C_6$alkylsulfamoyl, and N—$C_1$-$C_6$alkylcarbamoyl;

B is selected from formulae IIA and IIB;

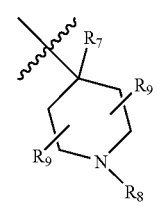

IIA

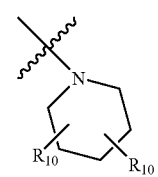

IIB $R_2$ is selected from $C_1$-$C_6$alkyl or $C_3$-$C_6$cycloalkyl, wherein $R_2$ may be optionally substituted with one, two, or three substituents selected, independently for each occurrence, from halogen, alkoxy, nitro, cyano, amino, and carboxyl;

$R_3$ and $R_4$ are each independently selected from the group consisting of hydrogen, $C_1$-$C_6$alkoxy, $C_1$-$C_6$alkyl, aryl, $C_3$-$C_6$cycloalkyl, halogen, heteroaryl, heterocyclyl, and hydroxyl, wherein $R_3$ or $R_4$, if not hydrogen, may be optionally substituted by one, two, or three substituents represented by $R_{10}$, or $R_3$ and $R_4$ are taken together with the carbon atom to which they are attached to form a four, five, or six membered heterocyclyl or $C_3$-$C_6$cycloalkyl optionally substituted by one, two, or three substituents each represented by $R_{10}$;

$R_7$ is selected from the group consisting of $C_1$-$C_6$alkoxy, $C_1$-$C_6$alkyl, cyano, halogen, hydrogen, and hydroxyl;

$R_8$ is selected from hydrogen or alkyl optionally substituted by one, two, or three substituents selected from the group consisting of halogen, hydroxyl, $C_1$-$C_6$alkylsulfonyl, $C_1$-$C_6$alkoxy, N—$C_1$-$C_6$alkylamino, N,N-di$C_1$-$C_6$alkylamino, cyano, carboxyl, sulfonamido, and $C_1$-$C_6$alkylsulfonamido;

$R_9$ is, independently for each occurrence, selected from the group consisting of hydrogen, halogen, hydroxyl, nitro, cyano, amino, sulfonyl, $C_1$-$C_6$alkylsulfonyl, sulfamoyl, sulfonamido, $C_1$-$C_6$alkylsulfonamido, carbamoyl, carboxyl, N—$C_1$-$C_6$alkylsulfamoyl, and N—$C_1$-$C_6$alkylcarbamoyl, $C_1$-$C_6$alkyl, $C_3$-$C_6$cycloalkyl, $C_1$-$C_6$alkylthio, and $C_1$-$C_6$alkoxy, wherein the alkyl, cycloalkyl or alkoxy is optionally substituted by one, two, or three substituents selected from the group consisting of halogen, hydroxyl, carboxy, cyano, amido, nitro, and amino;

$R_{10}$ is, independently for each occurrence, selected from the group consisting of halogen, hydroxyl, nitro, cyano, amino, sulfonyl, $C_1$-$C_6$alkylsulfonyl, sulfamoyl, sulfonamido, $C_1$-$C_6$alkylsulfonamido, carbamoyl, carboxy, N—$C_1$-$C_6$alkylsulfamoyl, and N—$C_1$-$C_6$alkylcarbamoyl, $C_1$-$C_6$alkyl, $C_3$-$C_6$cycloalkyl, $C_1$-$C_6$alkylthio, and $C_1$-$C_6$alkoxy, wherein the alkyl, cycloalkyl or alkoxy is optionally substituted by one, two, or three substituents selected from the group consisting of halogen, hydroxyl, carboxy, cyano, amido, nitro, and amino; and m is 0, 1, 2, 3, or 4;

or pharmaceutically acceptable salts or N-oxides thereof.

Also provided herein are methods of treating memory disorders, such as Alzheimer's disease, comprising administering to a subject in need thereof a therapeutically effective amount of a compound of formula I or II, or a pharmaceutically acceptable salt or N-oxides thereof. Also contemplated herein are compositions that include a compound represented by formula I or II and e.g., a pharmaceutically acceptable excipient.

The disclosure further provides methods of modulating activity of one or more 5-HT receptors comprising, for example, exposing said receptor to a disclosed compound.

Also provided herein are methods of treating a disease associated with expression or activity of one or more 5-HT receptors in a subject comprising administering to the patient a therapeutically effective amount of a disclosed compound. For example, provided herein are methods of treating Alzheimer's disease, Parkinson's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression comprising administering a compound represented by formula I and/or II. Also provided are compounds represented by formulas I and II for use in therapy and/or for the manufacture of a medicament for the treatment of disease associated with 5-HT receptors.

DEFINITIONS

Certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

"Treating" includes any effect, e.g., lessening, reducing, modulating, or eliminating, that results in the improvement of the condition, disease, disorder and the like.

The term "aldehyde" or "formyl" as used herein refers to the radical —CHO.

The term "alkanoyl" as used herein refers to a radical —O—CO-alkyl.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{10}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). Exemplary alkoxy groups include, but are not limited to, groups with an alkyl, alkenyl or alkynyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. In certain embodiments, alkyl refers to $C_1$-$C_6$ alkyl. In certain embodiments, cycloalkyl refers to $C_3$-$C_6$cycloalkyl.

Alkyl, alkenyl and alkynyl groups can, in some embodiments, be optionally be substituted with or interrupted by at least one group selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" or "amido" as used herein refers to a radical of the form —$R_aC(O)N(R_b)$—, —$R_aC(O)N(R_b)R_c$—, or —$C(O)NR_bR_c$, wherein $R_a$, $R_b$ and $R_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "carboxamido" refers to the structure —$C(O)NR_bR_c$.

The term "amidino" as used herein refers to a radical of the form —$C(=NR)NR'R''$ where R, R', and R'' can each independently be selected from alkyl, alkenyl, alkynyl, amide, aryl, arylalkyl, cyano, cycloalkyl, haloalkyl, heteroaryl, heterocyclyl, hydroxyl, ketone and nitro.

The term "amine" or "amino" as used herein refers to a radical of the form —$NR_dR_e$, —$N(R_d)R_e$—, or —$R_eN(R_d)R_f$— where $R_d$, $R_e$, and $R_f$ are independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amino can be attached to the parent molecular group through the nitrogen, $R_d$, $R_e$ or $R_f$. The amino also may be cyclic, for example any two of Rd, Re or Rf may be joined together or with the N to form a 3- to 12-membered ring, e.g., morpholino or piperidinyl. The term amino also includes the corresponding quaternary ammonium salt of any amino group, e.g., —[N(Rd)(Re)(Rf)]+. Exemplary amino groups include aminoalkyl groups, wherein at least one of $R_d$, $R_e$, or $R_f$ is an alkyl group.

The term "aryl" as used herein refers to refers to a mono-, bi-, or other multi-carbocyclic, aromatic ring system. In certain embodiments, aryl refers to a monocyclic and/or bicyclic, 5 to 6 membered ring. The aromatic ring may be substituted at one or more ring positions with substituents selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl.

The term "arylalkyl" as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms. For example, "phenylalkyl" includes phenyl$C_4$alkyl, benzyl, 1-phenylethyl, 2-phenylethyl, etc.

The term "azido" as used herein refers to the radical —$N_3$.

The term "carbamate" as used herein refers to a radical of the form —$R_g$OC(O)N($R_h$)—, —$R_g$OC(O)N($R_h$)$R_i$—, or —OC(O)N$R_h R_i$, wherein $R_g$, $R_h$ and $R_i$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, sulfide, sulfonyl, and sulfonamide. Exemplary carbamates include, but are not limited to, arylcarbamates or heteroaryl carbamates, e.g., wherein at least one of $R_g$, $R_h$ and $R_i$ are independently selected from aryl or heteroaryl, such as phenyl and pyridinyl.

The term "carbonyl" as used herein refers to the radical —C(O)—.

The term "carboxamido" as used herein refers to the radical —C(O)NRR', where R and R' may be the same or different. R and R' may be selected from, for example, alkyl, aryl, arylalkyl, cycloalkyl, formyl, haloalkyl, heteroaryl and heterocyclyl.

The term "carboxy" as used herein refers to the radical —COOH or its corresponding salts, e.g. —COONa, etc.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged bicyclic hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclohexenes, cyclopentanes, cyclopentenes, cyclobutanes and cyclopropanes. Cycloalkyl groups may be substituted with alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups. In certain embodiments, cycloalkyl refers to $C_3$-$C_6$ alkyl.

The term "ether" refers to a radical having the structure —$R_l$O—$R_m$—, where $R_l$ and $R_m$ can independently be alkyl, aryl, cycloalkyl, heterocyclyl, or ether. The ether can be attached to the parent molecular group through $R_l$ or $R_m$. Exemplary ethers include, but are not limited to, alkoxyalkyl and alkoxyaryl groups. Ether also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms.

The terms "heteroaryl" as used herein refers to a 5-15 membered mono-, bi-, or other multi-cyclic, aromatic ring system containing one or more heteroatoms, for example one to four heteroatoms, such as nitrogen, oxygen, and sulfur. In certain embodiments, heteroaryl refers to a mono or bicyclic, five or 6 membered ring containing 1, 2, or 3 heteroatoms. Heteroaryls can also be fused to non-aromatic rings. The heteroaryl ring may be substituted at one or more positions with such substituents as described above, as for example, alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Illustrative examples of heteroaryl groups include, but are not limited to, acridinyl, benzimidazolyl, benzofuryl, benzothiazolyl, benzothienyl, benzoxazolyl, carbazolyl, carbolinyl, cinnolinyl, furazanyl, furyl, imidazolyl, indazolyl, indolizinyl, indolyl, isobenzofuryl, isoindolyl, isoquinolinyl, isothiazolyl, isoxazolyl, naphthyridinyl, oxadiazolyl, oxazolyl, phenanthridinyl, phenanthrolinyl, phenarsazinyl, phenazinyl, phenothiazinyl, phenoxazinyl, phthalazinyl, pteridinyl, purinyl, pyrazinyl, pyrazolyl, pyrazyl, pyridazinyl, pyridinyl, pyrimidilyl, pyrimidyl, pyrrolyl, quinolinyl, quinolizinyl, quinoxalinyl, quinoxaloyl, quinazolinyl, tetrazolyl, thiadiazolyl, thianthrenyl, thiazolyl, thienyl, thiophenyl, triazinyl, (1,2,3)- and (1,2,4)-triazolyl, and the like. Exemplary heteroaryl groups include, but are not limited to, a monocyclic aromatic ring, wherein the ring comprises 2 to 5 carbon atoms and 1 to 3 heteroatoms.

The terms "heterocyclyl" or "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. The heterocyclic ring may be substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "heterocycloalkyl" is art-recognized and refers to a saturated heterocyclyl group as defined above.

The term "heterocyclylalkoxy" as used herein refers to a heterocyclyl attached to an alkoxy group.

The term "heterocyclyloxyalkyl" refers to a heterocyclyl attached to an oxygen (—O—), which is attached to an alkyl group.

The terms "hydroxy" and "hydroxyl" as used herein refers to the radical —OH.

The term "hydroxyalkyl" as used herein refers to a hydroxy radical attached to an alkyl group.

The term "imino" as used herein refers to the radical —C(=N)—R", where R" can be, for example, alkyl, alkenyl, alkynyl, aryl, arylalkyl, cycloalkyl, ether, haloalkyl, heteroaryl, heterocyclyl, and ketone.

The term "nitro" as used herein refers to the radical —$NO_2$.

The term "phenyl" as used herein refers to a 6-membered carbocyclic aromatic ring. The phenyl group can also be fused to a cyclohexane or cyclopentane ring. Phenyl can be substituted with one or more substituents including alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "phosphate" as used herein refers to the radical —$OP(O)(OR_{aa})_2$ or its anions. The term "phosphanato" refers to the radical —$P(O)(OR_{aa})_2$ or its anions. The term "phosphinato" refers to the radical —$PR_{aa}(O)(OR_{aa})$ or its anion, where each $R_{aa}$ can be selected from, for example, alkyl, alkenyl, alkynyl, aryl, arylalkyl, cycloalkyl, hydrogen, haloalkyl, heteroaryl, and heterocyclyl.

The term "sulfate" as used herein refers to the radical —$OS(O)(OR_{aa})_2$ or its anions, where $R_{aa}$ is defined above.

The term "sulfonamide" or "sulfonamido" as used herein refers to a radical having the structure —$N(R_r)$—$S(O)_2$—$R_s$— or —$S(O)_2$—$N(R_r)R_s$, where $R_r$ and $R_s$ can be, for example, hydrogen, alkyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl), etc.

The term "sulfonyl" as used herein refers to a radical having the structure $R_uSO_2$—, where $R_u$ can be alkyl, aryl, cycloalkyl, and heterocyclyl, e.g., alkylsulfonyl. The term "alkylsulfonyl" as used herein refers to an alkyl group attached to a sulfonyl group.

The term "sulfide" as used herein refers to the radical having the structure $R_zS$—, where $R_z$ can be alkoxy, alkyl, alkenyl, alkynyl, amide, amino, aryl, arylalkyl, carbamate, carboxy, cycloalkyl, ester, ether, formyl, haloalkyl, heteroaryl, heterocyclyl, and ketone. The term "alkylsulfide" as used herein refers to an alkyl group attached to a sulfur atom. Exemplary sulfides include "thio," which as used herein refers to an —SH radical.

The term "thiocarbonyl" or "thiocarboxy" as used herein refers to compounds and moieties which contain a carbon connected with a double bond to a sulfur atom.

"Pharmaceutically or pharmacologically acceptable" include molecular entities and compositions that do not produce an adverse, allergic or other untoward reaction when administered to an animal, or a human, as appropriate. "For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include to any animal, including mammals, such as, for example, mice, rats, other rodents, rabbits, dogs, cats, swine, cattle, sheep, horses, or primates, and humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of 5-HT4 receptors is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms associated with a disease associated with 5-HT4 receptors.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, for example, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be used in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (3-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the invention contains an alcohol functional group, a prodrug can be formed by the replacement of the hydrogen atom of the alcohol group with a group such as $(C_1-C_6)$alkanoyloxymethyl, 1-$((C_1-C_6)$alkanoyloxy) ethyl, 1-methyl-1-$((C_1-C_6)$alkanoyloxy)ethyl $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$ alkanoyl, arylacyl and α-aminoacyl, or α-aminoacyl-α-aminoacyl, where each α-aminoacyl group is independently selected from the naturally occurring L-amino acids, P(O) $(OH)_2$, —P(O)(O$_{(C_1-C_6)}$alkyl)$_2$ or glycosyl (the radical resulting from the removal of a hydroxyl group of the hemi-acetal form of a carbohydrate).

If a compound of the invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino, morpholino, piperidin-1-yl or pyrrolidin-1-yl.

The disclosure provides, at least in part, compounds represented by formula I, as depicted below. Also contemplated herein are compositions that include a compound represented by formula I and e.g., a pharmaceutically acceptable carrier.

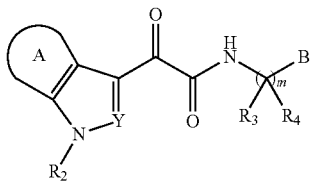

I wherein Y is N or CH;

A is aryl or hetoroaryl optionally substituted with one, two, three, or four substituents independently, for each occurrence, selected from the group consisting of halogen, hydroxyl, alkyl, haloalkyl, cycloalkyl, alkoxy, nitro, cyano, amino, sulfonyl, alkylsulfonyl, sulfamoyl, carbamoyl, carboxyl, N-alkylsulfamoyl, and N-alkylcarbamoyl;

B is selected from formulae IA, IB, or IC;

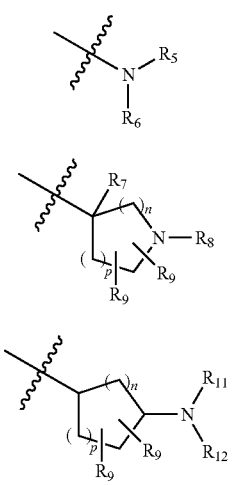

$R_2$ is selected from alkyl or cycloalkyl, wherein $R_2$ may be optionally substituted with one, two, or three substituents selected, independently for each occurrence, from the group consisting of halogen, alkoxy, nitro, cyano, amino, and carboxyl;

$R_3$ and $R_4$ are each independently selected from the group consisting of hydrogen, alkoxy, alkyl, aryl, cycloalkyl, halogen, heteroaryl, heterocyclyl, and hydroxyl, wherein $R_3$ or $R_4$, if not hydrogen, may be optionally substituted by one, two, or three substituents represented by $R_{10}$, or $R_3$ and $R_4$ are taken together with the carbon atom to which they are attached to form a heterocyclyl or cycloalkyl optionally substituted by one, two, or three substituents each represented by $R_{10}$;

$R_5$ and $R_6$ are each independently selected from the group consisting of alkyl, aryl, cycloalkyl, heteroaryl, heterocyclyl, and hydrogen, wherein $R_5$ or $R_6$, if not hydrogen, may be optionally substituted by one, two, or three substituents each represented by $R_{10}$, or $R_5$ and $R_6$ are taken together with the nitrogen atom to which they are attached to form a heterocyclyl optionally substituted by one, two, or three substituents each independently represented by $R_{10}$;

$R_{11}$ and $R_{12}$ are each independently selected from the group consisting of alkyl, aryl, cycloalkyl, heteroaryl, heterocyclyl, and hydrogen, wherein $R_{11}$ or $R_{12}$, if not hydrogen, may be optionally substituted by one, two, or three substituents each represented by $R_{10}$, or $R_{11}$ and $R_{12}$ are taken together with the nitrogen atom to which they are attached to form a heterocyclyl optionally substituted by one, two, or three substituents each independently represented by $R_{10}$;

$R_7$ is selected from the group consisting of alkoxy, alkyl, cyano, halogen, hydrogen, and hydroxyl;

$R_8$ is selected from hydrogen or alkyl optionally substituted by one, two, or three substituents selected from the group consisting of halogen, hydroxyl, alkylsulfonyl, alkoxy, N-alkylamino, N,N-dialkylamino, cyano, carboxyl, sulfonamido, and alkylsulfonamido;

$R_9$ is, independently for each occurrence, selected from the group consisting of hydrogen, halogen, hydroxyl, nitro, cyano, amino, sulfonyl, alkylsulfonyl, sulfamoyl, sulfonamido, alkylsulfonamido, carbamoyl, carboxyl, N-alkylsulfamoyl, N-alkylcarbamoyl, alkyl, cycloalkyl, alkylthio, and alkoxy, wherein the alkyl, cycloalkyl or alkoxy is optionally substituted by one, two, or three substituents selected from the group consisting of halogen, hydroxyl, carboxy, cyano, amido, nitro, and amino;

$R_{10}$ is selected from the group consisting of halogen, hydroxyl, nitro, cyano, amino, sulfonyl, alkylsulfonyl, sulfamoyl, sulfonamido, alkylsulfonamido, carbamoyl, carboxyl, N-alkylsulfamoyl, N-alkylcarbamoyl, alkyl, cycloalkyl, alkylthio, and alkoxy, wherein the alkyl, cycloalkyl or alkoxy is optionally substituted by one, two, or three substituents selected from the group consisting of halogen, hydroxyl, carboxy, cyano, amido, nitro, and amino;

m is 0, 1, 2, 3, or 4;
n is 0, 1, or 2; and
p is 0, 1 or 2;
or pharmaceutically acceptable salts or N-oxides thereof.
In one embodiment, A can have the formula

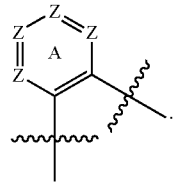

In another embodiment, each Z can be independently selected from CR$_1$ and N. Each R$_1$ may be selected from the group consisting of hydrogen, amino, nitro, cyano, halogen, alkoxy, and alkyl. For example, the alkoxy and alkyl groups can be optionally substituted by one, two, or three substituents selected from the group consisting of halogen, hydroxyl and cyano. In a further embodiment, each Z can be CH. In another embodiment, one Z can be N. In another embodiment, A is selected from phenyl and pyridinyl.

In one embodiment, A may be substituted by a substituent selected from the group consisting of amino, chloro, cyano, ethoxy, ethyl, fluoro, hydrogen, methoxy, methyl, nitro, and trifluoromethyl. In another embodiment, $R_2$ can be selected from the group consisting of methyl, ethyl, and propyl. For example, $R_2$ can be isopropyl. In another embodiment, $R_3$ and $R_4$ can each be hydrogen.

In one embodiment, B can be represented by formula IA. In some embodiments, $R_5$ and $R_6$ can each independently be alkyl. In other embodiments, $R_5$ and $R_6$ can each be independently selected from the group consisting of methyl, ethyl, and propyl, such as each of $R_5$ and $R_6$ can be ethyl.

In another embodiment, $R_5$ and $R_6$ may be taken together with the nitrogen atom to which they are attached to form a heterocyclyl selected from the group consisting of azetidinyl, piperazinyl, piperidinyl, pyrrolidinyl, and morpholino. In a further embodiment, the piperidinyl or pyrrolidinyl can be substituted with one or two substituents selected from the group consisting of methyl, ethyl, propyl, or butyl, each optionally substituted by hydroxyl, halogen, or carboxyl. In yet another embodiment, the piperidinyl or pyrrolidinyl may be substituted with one or two substituents selected from the group consisting of ethyl, 3-hydroxypropyl, propyl, and trifluoromethyl. In one embodiment, the heterocyclyl can be unsubstituted piperidinyl. In another embodiment, heterocyclyl is unsubstituted pyrrolidinyl. Variable m can be selected from 2, 3, or 4.

In another embodiment, B can be represented by formula IB. In some embodiments, n can be 1 or 2 and p can be 1 or 2. In other embodiments, n can be 2, p can be 1, and m can be 0 or 1.

In one embodiment, $R_7$ can be selected from the group consisting of hydrogen, fluoro, hydroxyl, and methyl. In another embodiment, $R_8$ may be selected from the group consisting of butyl, 4-(diethylamino)-4-oxobutyl, ethyl, fluoroethyl, fluoromethyl, hexyl, hydrogen, hydroxybutyl, hydroxyethyl, 2-hydroxy-3-(N-methylmethylsulfonamido)propyl, 3-hydroxybutyl, hydroxypropyl, methoxyethyl, methoxypropyl, methyl, 3-(dimethylamino)-3-oxopropyl, 2-methylpropyl, 3-(methylsulfonyl)propyl, methylsulfonamidoethyl, methylthioethyl, pentyl, propyl, and 3-(trifluoromethyl)propyl.

In one embodiment, B can be represented by formula IC. In one embodiment, $R_{11}$ and $R_{12}$ can each be independently selected from alkyl. In another embodiment, $R_{11}$ and $R_{12}$ may be taken together with the nitrogen atom to which they are attached to form a heterocyclyl selected from the group consisting of azetidinyl, morpholino, piperazinyl, piperidinyl, and pyrrolidinyl. In a further embodiment, $R_9$, independently for each occurrence, can be selected from the group consisting of butyl, ethyl, fluoroethyl, hydrogen, hydroxypropyl, isopropyl, methyl, and trifluoromethyl.

In one embodiment, $R_{10}$ can be selected from the group consisting of butyl, carboxy, cyano, diethylamino, 4-(diethylamino)-4-oxobutyl, dimethylamino, ethoxy, ethyl, fluoro, fluoroethyl, fluoromethyl, hexyl, hydrogen, hydroxybutyl, hydroxyethyl, hydroxymethyl, hydroxyl, 2-hydroxy-3-(N-methylmethylsulfonamido)propyl, 3-hydroxybutyl, 2-hydroxypropyl, 3-hydroxypropyl, methoxy, methoxymethyl, methoxypropyl, methyl, 3-(dimethylamino)-3-oxopropyl, 2-methylpropyl, methylsulfonyl, 3-(methylsulfonyl)propyl, propyl, and trifluoromethyl.

The disclosure provides, at least in part, compounds represented by formula II, as depicted below. Also contemplated herein are compositions that include a compound represented by formula II and e.g., a pharmaceutically acceptable carrier. As appropriate, each embodiment described above for formula I is understood to also be an embodiment of formula II.

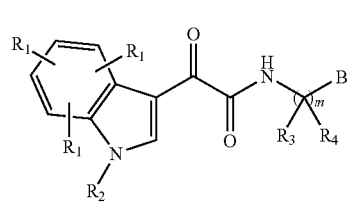

II wherein
$R_1$ is independently, for each occurrence, selected from the group consisting of halogen, hydroxyl, alkyl, haloalkyl, cycloalkyl, alkoxy, nitro, cyano, amino, sulfonyl, alkylsulfonyl, sulfamoyl, carbamoyl, carboxyl, N-alkylsulfamoyl, and N-alkylcarbamoyl;
B is selected from formulae IIA and IIB;

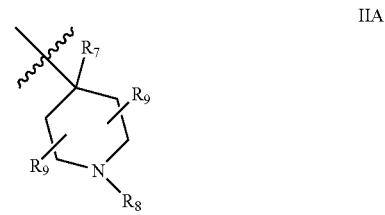

IIA

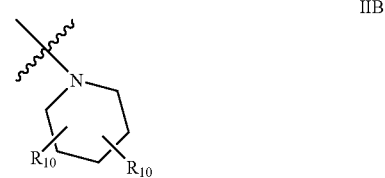

IIB $R_2$ is selected from alkyl or cycloalkyl, wherein $R_2$ may be optionally substituted with one, two, or three substituents selected, independently for each occurrence, from halogen, alkoxy, nitro, cyano, amino, and carboxyl;
$R_3$ and $R_4$ are each independently selected from the group consisting of hydrogen, alkoxy, alkyl, aryl, cycloalkyl, halogen, heteroaryl, heterocyclyl, and hydroxyl, wherein $R_3$ or $R_4$, if not hydrogen, may be optionally substituted by one, two, or three substituents represented by $R_{10}$, or $R_3$ and $R_4$ are taken together with the carbon atom to which they are attached to form a heterocyclyl or cycloalkyl optionally substituted by one, two, or three substituents each represented by $R_{10}$;
$R_7$ is selected from the group consisting of alkoxy, alkyl, cyano, halogen, hydrogen, and hydroxyl;
$R_8$ is selected from hydrogen or alkyl optionally substituted by one, two, or three substituents selected from the group consisting of halogen, hydroxyl, alkylsulfonyl, alkoxy, N-alkylamino, N,N-dialkylamino, cyano, carboxyl, sulfonamido, and alkylsulfonamido;
$R_9$ is, independently for each occurrence, selected from the group consisting of hydrogen, halogen, hydroxyl, nitro, cyano, amino, sulfonyl, alkylsulfonyl, sulfamoyl, sulfonamido, alkylsulfonamido, carbamoyl, carboxyl, N-alkylsulfamoyl, and N-alkylcarbamoyl, alkyl, cycloalkyl, alkylthio, and alkoxy, wherein the alkyl, cycloalkyl or alkoxy is optionally substituted by one, two, or three substituents selected from the group consisting of halogen, hydroxyl, carboxy, cyano, amido, nitro, and amino;

$R_{10}$ is, independently for each occurrence, selected from the group consisting of halogen, hydroxyl, nitro, cyano, amino, sulfonyl, alkylsulfonyl, sulfamoyl, sulfonamido, alkylsulfonamido, carbamoyl, carboxyl, N-alkylsulfamoyl, and N-alkylcarbamoyl, alkyl, cycloalkyl, alkylthio, and alkoxy, wherein the alkyl, cycloalkyl or alkoxy is optionally substituted by one, two, or three substituents selected from the group consisting of halogen, hydroxyl, carboxy, cyano, amido, nitro, and amino; and m is 0, 1, 2, 3, or 4;

or pharmaceutically acceptable salts or N-oxides thereof.

Contemplated compounds, and pharmaceutical compositions, comprising at least one compound, may be selected from the group consisting of: 2-(1-isopropyl-1H-indol-3-yl)-2-oxo-N-(3-(piperidin-1-yl)propyl)acetamide; 2-(1-isopropyl-1H-indol-3-yl)-2-oxo-N-(2-(piperidin-1-yl)ethyl)acetamide; N-(2-(diethylamino)ethyl)-2-(1-isopropyl-1H-indol-3-yl)-2-oxoacetamide; 2-(1-ethyl-1H-indol-3-yl)-2-oxo-N-(2-(piperidin-1-yl)ethyl)acetamide; 2-(1-sec-butyl-1H-indol-3-yl)-2-oxo-N-(2-(piperidin-1-yl)ethyl)acetamide; 2-(5-chloro-1-isopropyl-1H-indol-3-yl)-2-oxo-N-(2-(piperidin-1-yl)ethyl)acetamide; 2-(1-isopropyl-6-nitro-1H-indol-3-yl)-2-oxo-N-(2-(piperidin-1-yl)ethyl)acetamide; 2-(6-amino-1-isopropyl-1H-indol-3-yl)-2-oxo-N-(2-(piperidin-1-yl)ethyl)acetamide; 2-(6-amino-7-chloro-1-isopropyl-1H-indol-3-yl)-2-oxo-N-(2-(piperidin-1-yl)ethyl)acetamide; 2-(1-isopropyl-1H-indol-3-yl)-2-oxo-N-(2-(pyrrolidin-1-yl)ethyl)acetamide; 2-(1-isopropyl-5-methoxy-1H-indol-3-yl)-2-oxo-N-(2-(piperidin-1-yl)ethyl)acetamide; 2-(1-isopropyl-5-methyl-1H-indol-3-yl)-2-oxo-N-(2-(piperidin-1-yl)ethyl)acetamide; N-(1-(3-hydroxypropyl)piperidin-4-yl)-2-(1-isopropyl-1H-indol-3-yl)-2-oxoacetamide; 2-(1-isopropyl-1H-indol-3-yl)-2-oxo-N-(1-propylpiperidin-4-yl)acetamide; N-((1-isobutylpiperidin-4-yl)methyl)-2-(1-isopropyl-1H-indol-3-yl)-2-oxoacetamide; 2-(1-isopropyl-1H-indol-3-yl)-2-oxo-N-(2-(4-(trifluoromethyl)piperidin-1-yl)ethyl)acetamide; N-(1-butylpiperidin-4-yl)-2-(1-isopropyl-1H-indol-3-yl)-2-oxoacetamide; 2-(1-isopropyl-1H-indol-3-yl)-N-(1-(3-methoxypropyl)piperidin-4-yl)-2-oxoacetamide; 2-(1-isopropyl-1H-pyrrolo[2,3-b]pyridin-3-yl)-2-oxo-N-(2-(piperidin-1-yl)ethyl)acetamide; 2-(1-isopropyl-1H-indol-3-yl)-N-(1-(2-(methylsulfonamido)ethyl)piperidin-4-yl)-2-oxoacetamide; 2-(1-isopropyl-1H-indol-3-yl)-2-oxo-N-(2-(4-propylpiperidin-1-yl)ethyl)acetamide; N-(2-(4-(2-hydroxyethyl)piperidin-1-yl)ethyl)-2-(1-isopropyl-1H-indol-3-yl)-2-oxoacetamide; N-(2-(4-ethylpiperidin-1-yl)ethyl)-2-(1-isopropyl-1H-indol-3-yl)-2-oxoacetamide; and N-(2-(4-butylpiperidin-1-yl)ethyl)-2-(1-isopropyl-1H-indol-3-yl)-2-oxoacetamide and pharmaceutically acceptable salts or N-oxides thereof, and, in some embodiments, a pharmaceutically acceptable carrier.

Further contemplated compounds, and pharmaceutical compositions, comprising at least one compound, may be selected from the group consisting of: 2-(1-ethyl-1H-indol-3-yl)-2-oxo-N-(3-(piperidin-1-yl)propyl)acetamide; N-(2-(ethyl(methyl)amino)ethyl)-2-(1-isopropyl-1H-indol-3-yl)-2-oxoacetamide; 2-(1-sec-butyl-1H-indol-3-yl)-2-oxo-N-(3-(piperidin-1-yl)propyl)acetamide; 2-(1-isobutyl-1H-indol-3-yl)-2-oxo-N-(3-(piperidin-1-yl)propyl)acetamide; 2-(1-isopropyl-1H-indol-3-yl)-2-oxo-N-(3-(pyrrolidin-1-yl)propyl)acetamide; N-(3-(ethyl(methyl)amino)propyl)-2-(1-isopropyl-1H-indol-3-yl)-2-oxoacetamide; 2-(1-isobutyl-1H-indol-3-yl)-2-oxo-N-(2-(piperidin-1-yl)ethyl)acetamide; 2-(1-isopropyl-1H-indol-3-yl)-2-oxo-N-(2-(pyrrolidin-1-yl)ethyl)acetamide; (R)-2-(1-sec-butyl-1H-indol-3-yl)-2-oxo-N-(3-(piperidin-1-yl)propyl)acetamide; (S)-2-(1-sec-butyl-1H-indol-3-yl)-2-oxo-N-(3-(piperidin-1-yl)propyl) acetamide; (S)-2-(1-sec-butyl-1H-indol-3-yl)-2-oxo-N-(2-(piperidin-1-yl)ethyl)acetamide; (R)-2-(1-sec-butyl-1H-indol-3-yl)-2-oxo-N-(2-(piperidin-1-yl)ethyl)acetamide; 2-(4-hydroxy-1-isopropyl-1H-indol-3-yl)-2-oxo-N-(3-(piperidin-1-yl)propyl)acetamide; 2-(4-hydroxy-1-isopropyl-1H-indol-3-yl)-2-oxo-N-(2-(piperidin-1-yl)ethyl)acetamide; 2-(1-ethyl-4-hydroxy-1H-indol-3-yl)-2-oxo-N-(2-(piperidin-1-yl)ethyl)acetamide; 2-(6-amino-1-isopropyl-1H-indol-3-yl)-2-oxo-N-(3-(piperidin-1-yl)propyl)acetamide; 2-(5-amino-6-chloro-1-isopropyl-1H-indol-3-yl)-2-oxo-N-(3-(piperidin-1-yl)propyl)acetamide; 2-(6-amino-5-chloro-1-isopropyl-1H-indol-3-yl)-2-oxo-N-(2-(piperidin-1-yl)ethyl)acetamide; 2-(5-amino-6-chloro-1-isopropyl-1H-indol-3-yl)-2-oxo-N-(2-(piperidin-1-yl)ethyl)acetamide; 2-(1-isopropyl-1H-indol-3-yl)-N-(2-(4-methylpiperidin-1-yl)ethyl)-2-oxoacetamide; 2-(1-isopropyl-1H-pyrrolo[2,3-c]pyridin-3-yl)-2-oxo-N-(2-(piperidin-1-yl)ethyl)acetamide; 2-(1-isopropyl-1H-pyrrolo[3,2-b]pyridin-3-yl)-2-oxo-N-(2-(piperidin-1-yl)ethyl)acetamide; 2-(1-isopropyl-1H-pyrrolo[3,2-c]pyridin-3-yl)-2-oxo-N-(2-(piperidin-1-yl)ethyl)acetamide; 2-(4-isopropyl-4H-thieno[3,2-b]pyrrol-6-yl)-2-oxo-N-(2-(piperidin-1-yl)ethyl)acetamide; 2-(1-isopropyl-2-methyl-1H-indol-3-yl)-2-oxo-N-(2-(piperidin-1-yl)ethyl)acetamide; 2-(2-ethyl-1-isopropyl-1H-indol-3-yl)-2-oxo-N-(2-(piperidin-1-yl)ethyl)acetamide; 2-(1-isopropyl-1H-indol-3-yl)-N-(1-morpholinopropan-2-yl)-2-oxoacetamide; 2-(1-isopropyl-1H-indol-3-yl)-2-oxo-N-((1-propylpyrrolidin-3-yl)methyl)acetamide; N-((1-(dimethylamino)cyclopentyl)methyl)-2-(1-isopropyl-1H-indol-3-yl)-2-oxoacetamide; N-(1-ethylpiperidin-3-yl)-2-(1-isopropyl-1H-indol-3-yl)-2-oxoacetamide; N-((1-ethylpyrrolidin-2-yl)methyl)-2-(1-isopropyl-1H-indol-3-yl)-2-oxoacetamide; N-((4-hydroxy-1-methylpiperidin-4-yl)methyl)-2-(1-isopropyl-1H-indol-3-yl)-2-oxoacetamide; N-(3-(dimethylamino)cyclopentyl)-2-(1-isopropyl-1H-indol-3-yl)-2-oxoacetamide; N-(3-(dimethylamino)cyclohexyl)-2-(1-isopropyl-1H-indol-3-yl)-2-oxoacetamide; N-(2-(3-fluoropyrrolidin-1-yl)ethyl)-2-(1-isopropyl-1H-indol-3-yl)-2-oxoacetamide; N-(2-((2-fluoroethyl)(methyl)amino)ethyl)-2-(1-isopropyl-1H-indol-3-yl)-2-oxoacetamide; N-(2-(4-fluoropiperidin-1-yl)ethyl)-2-(1-isopropyl-1H-indol-3-yl)-2-oxoacetamide; N-(2-(3-hydroxypyrrolidin-1-yl)ethyl)-2-(1-isopropyl-1H-indol-3-yl)-2-oxoacetamide; 2-(1-isopropyl-1H-indol-3-yl)-N-(2-(3-(methylsulfonyl)pyrrolidin-1-yl)ethyl)-2-oxoacetamide; N-(2-(4-ethoxypiperidin-1-yl)ethyl)-2-(1-isopropyl-1H-indol-3-yl)-2-oxoacetamide; N-(2-(4-(dimethylamino)piperidin-1-yl)ethyl)-2-(1-isopropyl-1H-indol-3-yl)-2-oxoacetamide; N-(2-(4-ethylpiperazin-1-yl)ethyl)-2-(1-isopropyl-1H-indol-3-yl)-2-oxoacetamide; 2-(1-isopropyl-1H-indazol-3-yl)-2-oxo-N-(2-(piperidin-1-yl)ethyl)acetamide; 2-(1-(2-hydroxyethyl)-1H-indol-3-yl)-2-oxo-N-(2-(piperidin-1-yl)ethyl)acetamide; (R)—N-(2-(4-(2-hydroxy-3-(N-methylmethylsulfonamido)propyl)piperidin-1-yl)ethyl)-2-(1-isopropyl-1H-indol-3-yl)-2-oxoacetamide; 2-(1-isopropyl-1H-indol-3-yl)-N-(2-(4-(3-(methylsulfonyl)propyl)piperidin-1-yl)ethyl)-2-oxoacetamide; N-(3-(diethylamino)propyl)-2-(1-isopropyl-1H-indol-3-yl)-2-oxoacetamide; N-(4-(diethylamino)cyclohexyl)-2-(1-isopropyl-1H-indol-3-yl)-2-oxoacetamide; N-(1-ethylpiperidin-4-yl)-2-(1-isopropyl-1H-indol-3-yl)-2-oxoacetamide; 2-(1-isopropyl-1H-indol-3-yl)-N-(3-(4- methylpiperidin-1-yl)propyl)-2-oxoacetamide; N-(3-(4-ethylpiperidin-1-yl)propyl)-2-(1-isopropyl-1H-indol-3-yl)-2-oxoacetamide; 2-(1-isopropyl-1H-indol-3-yl)-2-oxo-N-(3-(4-propylpiperidin-1-yl)propyl)acetamide; 2-(1-isopropyl-1H-indol-3-yl)-2-oxo-N-((1-propylpiperidin-4-yl)methyl)acetamide; N-((1-butylpiperidin-4-yl)methyl)-2-(1-isopropyl-1H-indol-3-yl)-2-oxoacetamide; N-((4-chloro-1-methylpiperidin-4-yl)methyl)-2-(1-isopropyl-1H-indol-3-yl)-2-oxoacetamide; N-((1,4-dimethylpiperidin-4-yl)methyl)-2-(1-isopropyl-1H-indol-3-yl)-2-oxoacetamide; N-(2-(4-(dimethylamino)cyclohexyl)ethyl)-2-(1-isopropyl-1H-indol-3-yl)-2-oxoacetamide; N-(2-(4-(ethylamino)cyclohexyl)ethyl)-2-(1-isopropyl-1H-indol-3-yl)-2-oxoacetamide; N-((4-(dimethylamino)cyclohexyl)methyl)-2-(1-isopropyl-1H-indol-3-yl)-2-oxoacetamide; N-((4-(diethylamino)cyclohexyl)methyl)-2-(1-isopropyl-1H-indol-3-yl)-2-oxoacetamide; 2-(1-isopropyl-1H-indol-3-yl)-N-(6-isopropylpiperidin-3-yl)-2-oxoacetamide; N-(6-butylpiperidin-3-yl)-2-(1-isopropyl-1H-indol-3-yl)-2-oxoacetamide; N-(6-(3-hydroxypropyl)piperidin-3-yl)-2-(1-isopropyl-1H-indol-3-yl)-2-oxoacetamide; 2-(1-(1-chloroethyl)-1H-indol-3-yl)-N-(2-(diethylamino)ethyl)-2-oxoacetamide; N-(2-(diethylamino)ethyl)-2-oxo-2-(1-(2-oxopropyl)-1H-indol-3-yl)acetamide; 2-(1-(1-cyanoethyl)-1H-indol-3-yl)-N-(2-(diethylamino)ethyl)-2-oxoacetamide; N-(2-(4-(3-hydroxypropyl)piperidin-1-yl)ethyl)-2-(1-isopropyl-1H-indol-3-yl)-2-oxoacetamide; N-((1-(3-hydroxypropyl)piperidin-4-yl)methyl)-2-(1-isopropyl-1H-indol-3-yl)-2-oxoacetamide; N-(1-(3-hydroxybutyl)piperidin-4-yl)-2-(1-isopropyl-1H-indol-3-yl)-2-oxoacetamide; N-((1-ethyl-4-hydroxypiperidin-4-yl)methyl)-2-(1-isopropyl-1H-indol-3-yl)-2-oxoacetamide; N-((4-hydroxy-1-propylpiperidin-4-yl)methyl)-2-(1-isopropyl-1H-indol-3-yl)-2-oxoacetamide; N-((1-butyl-4-hydroxypiperidin-4-yl)methyl)-2-(1-isopropyl-1H-indol-3-yl)-2-oxoacetamide; N,N-diethyl-4-(4-(2-(1-isopropyl-1H-indol-3-yl)-2-oxoacetamido)piperidin-1-yl)butanamide; 2-(1-isopropyl-1H-indol-3-yl)-N-(3-morpholinopropyl)-2-oxoacetamide; 2-(1-isopropyl-1H-indol-3-yl)-2-oxo-N-(4-(piperidin-1-yl)butyl)acetamide; 2-(1-isopropyl-1H-indol-3-yl)-2-oxo-N-(1-pentylpiperidin-4-yl)acetamide; N-(1-hexylpiperidin-4-yl)-2-(1-isopropyl-1H-indol-3-yl)-2-oxoacetamide; 3-(4-(2-(1-isopropyl-1H-indol-3-yl)-2-oxoacetamido)piperidin-1-yl)-N,N-dimethylpropanamide; 2-(3-(2-oxo-2-(2-(piperidin-1-yl)ethylamino)acetyl)-1H-indol-1-yl)acetic acid; 3-(3-(2-oxo-2-(2-(piperidin-1-yl)ethylamino)acetyl)-1H-indol-1-yl)propanoic acid; 2-(3-(2-oxo-2-(2-(piperidin-1-yl)ethylamino)acetyl)-1H-indol-1-yl)propanoic acid; 1-(2-(2-(1-isopropyl-1H-indol-3-yl)-2-oxoacetamido)ethyl)piperidine-4-carboxylic acid; N-(3-(4-(2-hydroxyethyl)piperidin-1-yl)propyl)-2-(1-isopropyl-1H-indol-3-yl)-2-oxoacetamide; 2-(1-isopropyl-1H-indol-3-yl)-N-(1-(2-methoxyethyl)piperidin-4-yl)-2-oxoacetamide; 2-(1-isopropyl-1H-indol-3-yl)-N-(2-(4-(methoxymethyl)piperidin-1-yl)ethyl)-2-oxoacetamide; N-(2-(4-(2-hydroxypropyl)piperidin-1-yl)ethyl)-2-(1-isopropyl-1H-indol-3-yl)-2-oxoacetamide; 2-(5-fluoro-1-isopropyl-1H-indol-3-yl)-2-oxo-N-(2-(piperidin-1-yl)ethyl)acetamide; 2-(5-fluoro-1-methyl-1H-indol-3-yl)-2-oxo-N-(2-(piperidin-1-yl)ethyl)acetamide; 2-(1-methyl-1H-indol-3-yl)-2-oxo-N-(2-(piperidin-1-yl)ethyl)acetamide; 2-(1-isopropyl-1H-indol-3-yl)-N-(1-(2-(methylthio)ethyl)piperidin-4-yl)-2-oxoacetamide; and 2-(1-isopropyl-1H-indol-3-yl)-2-oxo-N-(1-(4,4,4-trifluorobutyl)piperidin-4-yl)acetamide and pharmaceutically acceptable salts or N-oxides thereof, and, in some embodiments, a pharmaceutically acceptable carrier.

The present disclosure also provides pharmaceutical compositions comprising compounds as disclosed herein formulated together with one or more pharmaceutically acceptable carriers. These formulations include those suitable for oral, rectal, topical, buccal and parenteral (e.g., subcutaneous, intramuscular, intradermal, or intravenous) administration, although the most suitable form of administration in any given case will depend on the degree and severity of the condition being treated and on the nature of the particular compound being used.

The invention further provides methods of modulating activity of one or more 5-$HT_4$ receptors comprising exposing said receptor to a compound of the invention. The invention further provides methods of treating a disease associated with expression or activity of one or more 5-$HT_4$ receptors in a patient comprising administering to the patient a therapeutically effective amount of a compound of the invention.

One embodiment of the invention provides a method of treating Alzheimer's disease, Parkinson's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression comprising administering to a subject in need thereof a therapeutically effective amount of a compound of the invention. The methods disclosed herein may involve treating a memory disorder, such as Alzheimer's disease.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Compositions for inhalation or insufflation include solutions and suspensions in pharmaceutically acceptable, aqueous or organic solvents, or mixtures thereof, and powders.

Advantageously, the invention also provides kits for use by a consumer having, or at risk of having, a disease or condition associated with 5-HT4 receptors. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil, such as, for example a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet may be such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds of the present invention can be prepared in a number of ways well known to one skilled in the art of organic synthesis. More specifically, compounds of the invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Schemes 1-4 depict methods for making exemplary compounds of the invention as described below.

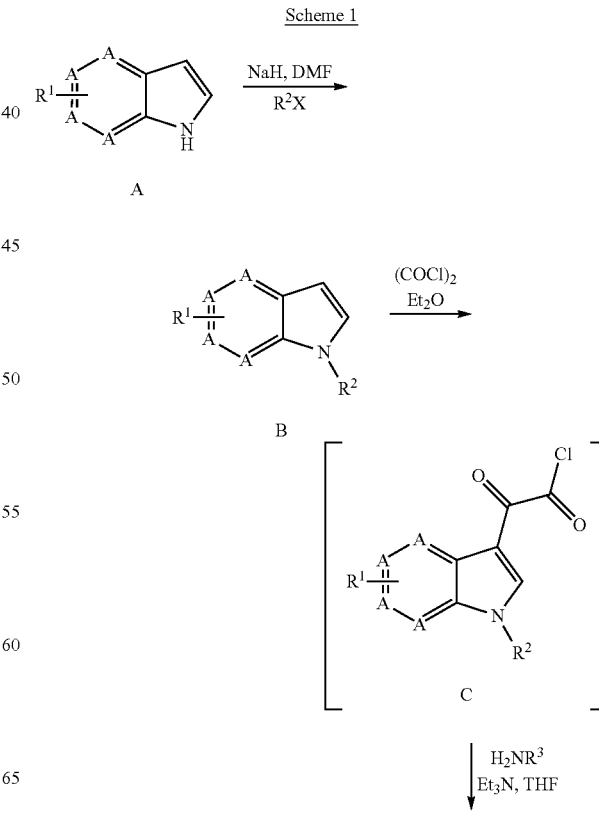

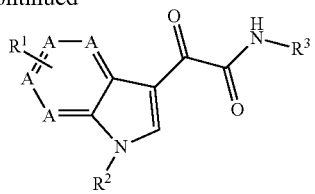
D
Scheme 2
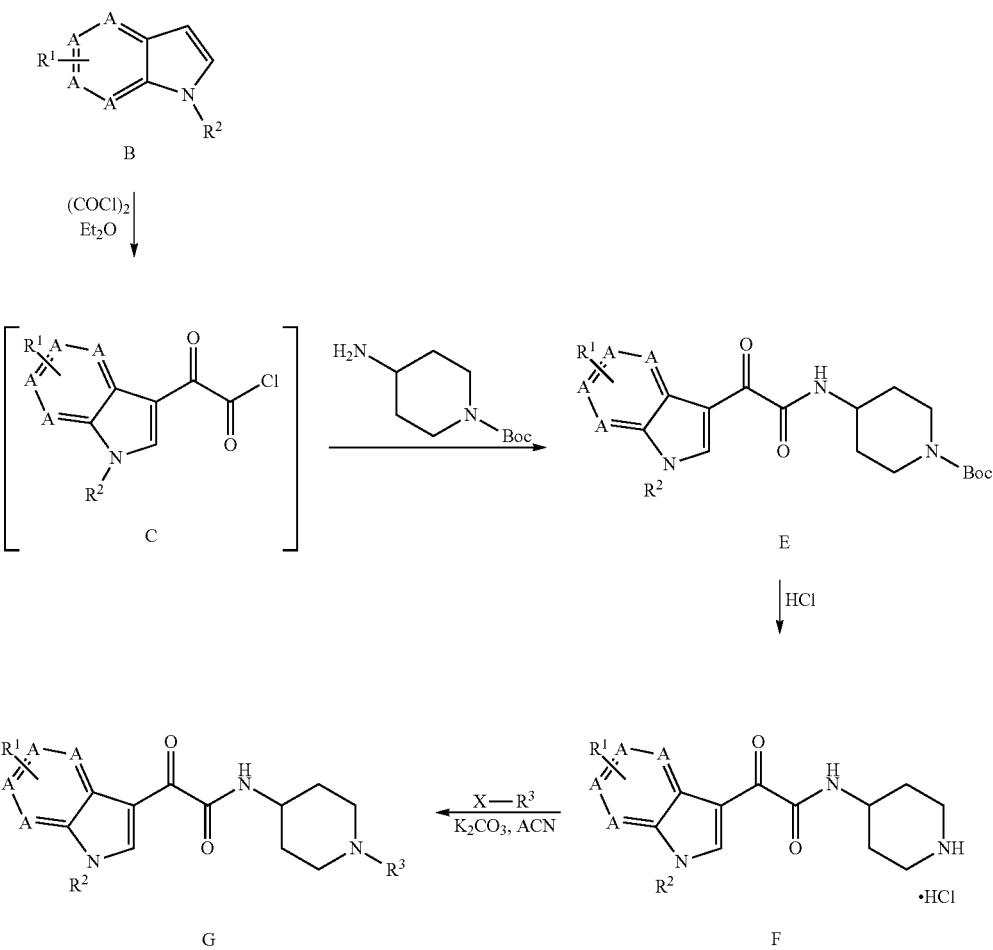
Scheme 3
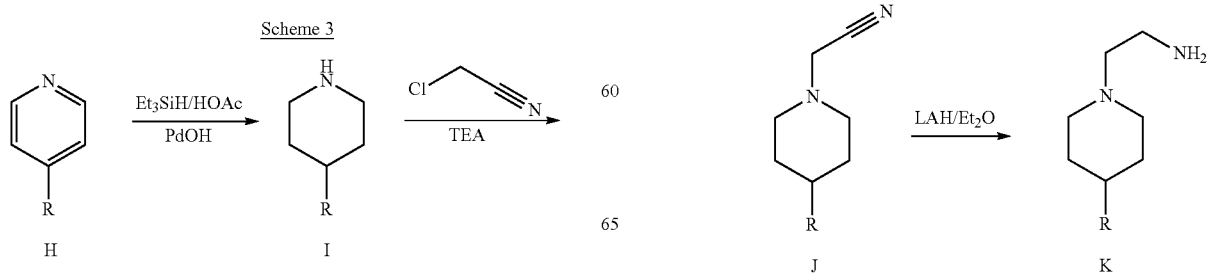

Scheme 4

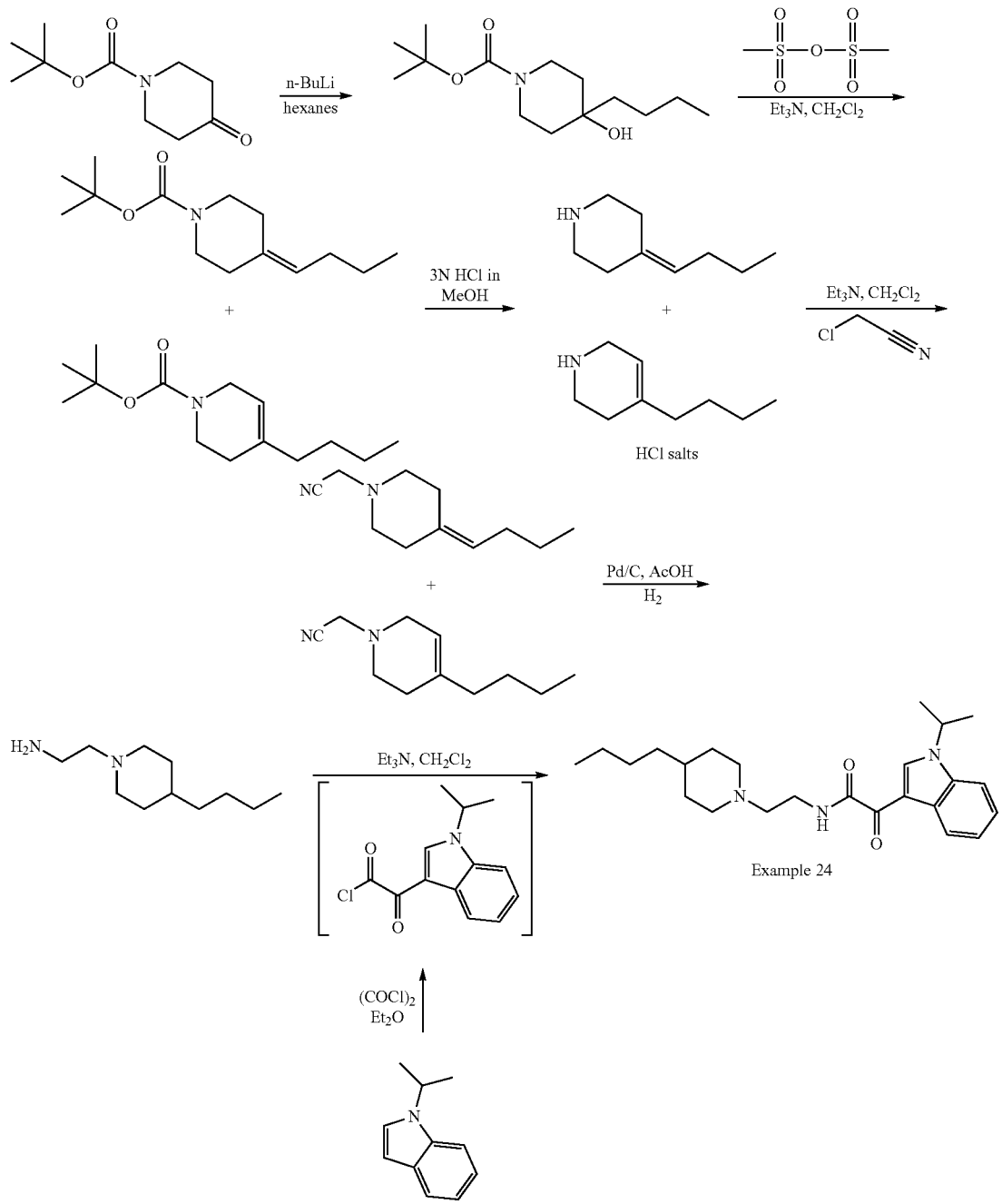

Example 24

A: General Procedure for Step 1 of Scheme 1

A solution of heterocycle A (1 eq.) in DMF at 0° C. was treated with NaH (2 eq.) portion wise. The reaction mixture was warmed to RT over a 30 min. period. The appropriate alkyl halide (1.5 eq.) was added to the reaction mixture at RT and the mixture was stirred for 14 h. The reaction mixture was then treated with H₂O and extracted with EtOAc. The combined organic layer was washed with sat. NaHCO₃ and H₂O, and dried over anhydrous Na₂SO₄. The solvent was removed under reduced pressure and the crude material was purified on silica gel to collect compounds of formula B.

B: General Procedure for Steps 2 and 3 of Scheme 1

A solution of heterocycle B (1 eq.) in Et₂O was cooled to 0° C. and treated dropwise with oxalyl chloride (1.2 eq.). The reaction was gradually warmed to RT over a 3 h period and then concentrated under reduced pressure. The resulting compound of formula C was dissolved in DCM, cooled to 0° C. and treated with a solution of the appropriate amine (1.2 eq.) and triethylamine (6.0 eq.) in DCM. The reaction mixture was allowed to warm to RT and stirred for 14 h. The reaction mixture was concentrated under reduced pressure and the crude material was purified on silica to provide compounds of formula D.

C: General Procedure for Steps 1 and 2 of Scheme 2

A solution of heterocycle B (1 eq.) in Et$_2$O was cooled to 0° C. and treated dropwise with oxalyl chloride (1.2 eq.). The reaction was gradually warmed to RT over a 3 h period and then concentrated under reduced pressure. The resulting compound of formula C was dissolved in DCM, cooled to 0° C. and treated with a solution of the appropriate amine (1.2 eq.) and triethylamine (6.0 eq.) in DCM. The reaction mixture was allowed to warm to RT and stirred for 14 h. The reaction mixture was concentrated under reduced pressure and the crude material was purified on silica to provide compounds of formula E.

D: General Procedure for Step 3 of Scheme 2

Protected amine E (1 eq.) was treated with 3 N HCl in MeOH (5 eq.) and stirred at RT for 30 min. The reaction mixture was concentrated under reduced pressure to afford salts of formula F.

E: General Procedure for Step 4 of Scheme 2

A solution of salt F (1 eq.) in acetonitrile was treated with K$_2$CO$_3$ (3 eq.) and the appropriate halide (2 eq.). The reaction mixture was stirred at 65° C. for 72 h and was then concentrated under reduced pressure. The crude material was purified on silica gel to provide compounds of formula G.

F: General Procedure for Step 1 of Scheme 3

Substituted pyridine H (1 eq.) was treated with triethylsilane (20 eq.), PdOH (20 wt. % Pd on activated carbon, 0.20 eq.) and acetic acid (cat. 2 drops) in a 40 mL vial. Gas evolution immediately started and the vial was capped until there was no visible gas evolution (~30 min.). The reaction mixture was then heated at 50° C. for 14 h with shaking. The crude reaction mixture containing I was used directly in the next step.

G: General Procedure for Step 2 of Scheme 3

The crude triethylsilane solution of I was filtered and then treated with 2-chloroacetonitrile (2 eq.), K$_2$CO$_3$ (2 eq.) and heated at 65° C. for 14 h. The crude reaction mixture was filtered to yield the desired alkylated piperidine J. The crude reaction mixture was used directly in the reduction.

H: General Procedure for Step 3 of Scheme 3

The crude solution of J was added carefully to a slurry of LiAlH$_4$ (8.3 eq.) in Et$_2$O and stirred at RT under argon for 14 h. The crude reaction mixture was cooled to 0° C. and treated dropwise with 10% aqueous NaOH and stirred for 30 min. The cooled mixture was treated with H$_2$O to provide a thick precipitate. The mixture was then treated with Et$_2$O, stirred and filtered. The filter cake was washed with Et$_2$O. The combined ether layer was concentrated under reduced pressure to provide a concentrated solution in Et$_2$O/H$_2$O that was acidified to pH 2 with 1 N HCl. The mixture was concentrated under reduced pressure to provide compounds of formula K.

Example 1

2-(1-Isopropyl-1H-indol-3-yl)-2-oxo-N-(3-(piperidin-1-yl)propyl)acetamide hydrochloride

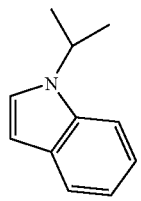

N-Isopropylindole

The title compound was prepared according to general procedure A described in Scheme 1. A solution of indole (5 g, 43 mmol) in DMF (60 mL) at to 0° C. was treated with NaH (60% in mineral oil, 3.4 g, 86 mmol) in 4 portions providing a slurry that was gradually warmed to RT over a 30 min period. Isopropyl iodide (1.1 g, 64 mmol) was added to the reaction mixture at RT and the mixture was stirred for 14 h. The reaction mixture was then treated with H$_2$O (50 mL) and extracted with EtOAc (3×50 mL). The combined organic extracts were washed with sat. NaHCO$_3$ (1×50 mL), H$_2$O (1×50 mL) and dried over anhydrous Na$_2$SO$_4$. The solvent was removed under reduced pressure and the crude material was purified on silica gel (Biotage, 0-10% EtOAc/Hexanes, 30 min.) to provide N-isopropylindole as a colorless oil (2.9 g, 43% yield).

2-(1-Isopropyl-1H-indol-3-yl)-2-oxo-N-(3-(piperidin-1-yl)propyl)acetamide hydrochloride

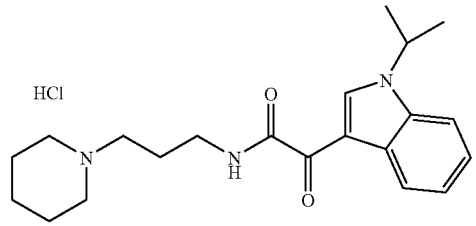

The title compound was prepared according to general procedure B described in Scheme 1. A solution of N-isopropylindole (480 mg, 3 mmol) in diethylether (10 mL) was cooled to 0° C. and treated dropwise with oxalyl chloride (303 μL, 3.5 mmol). The reaction was gradually warmed to RT over a 3 h period affording a yellow precipitate. The reaction mixture was concentrated under reduced pressure and the resulting yellow solid was dissolved in DCM (15 mL), cooled to 0° C. and treated with a solution of 1-piperidinepropanamine (313 g, 2 mmol) and triethylamine (334 μL, 2.4 mmol) in THF (10 mL). The reaction mixture was allowed to warm to RT and stirred for 14 h. The reaction mixture was concentrated under reduced pressure and the crude material was purified on silica gel (Biotage, 0-30% MeOH/DCM) and then converted to the HCl salt to provide the title compound as a purple solid (112 mg, 100% yield). $^1$H NMR (400 MHz, CDCl$_3$): δ 12.19 (NH$^+$, br s, 1H), 9.02 (s, 1H), 8.44 (dd, 1H), 7.95 (br t, 1H), 7.44 (m, 1H), 7.33 (m, 2H), 4.71 (m, 1H), 3.54 (m, 4H), 3.00 (m, 2H), 2.59 (m, 2H), 2.29 (m, 4H), 1.9-1.7 (m, 3H), 1.61 (d, 6H) 1.39 (m, 1H); MS (ESI) m/z: Calculated for C$_{21}$H$_{29}$N$_3$O$_2$: 355.2. Found: 356.3 (M+H)$^+$.

Example 2

2-(1-Isopropyl-1H-indol-3-yl)-2-oxo-N-(2-(piperidin-1-yl)ethyl)acetamide hydrochloride

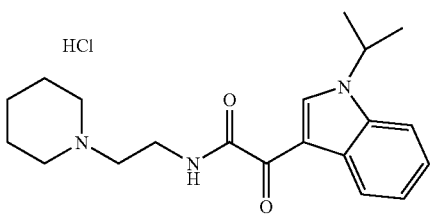

The title compound was prepared according to general procedure B described in Scheme 1 from N-isopropylindole and 1-piperidimethylamine (682 mg, 91% yield): $^1$H NMR (400 MHz, CDCl$_3$): δ 12.45 (NH$^+$, br s, 1H), 8.96 (s, 1H), 8.46 (m, 1H), 8.44 (m, 1H), 7.42 (m, 1H), 7.35 (m, 2H), 4.71 (m, 1H), 4.00 (q, 2H), 3.62 (d, 2H), 3.20 (q, 2H), 2.73 (q, 2H), 2.34 (q, 2H), 1.89 (m, 3H), 1.61 (d, 6H), 1.40 (m, 1H); MS (ESI) m/z: Calculated for C$_{20}$H$_{27}$N$_3$O$_2$: 341.2. Found: 342.3 (M+H)$^+$.

Example 3

N-(2-(Diethylamino)ethyl)-2-(1-isopropyl-1H-indol-3-yl)-2-oxoacetamide hydrochloride

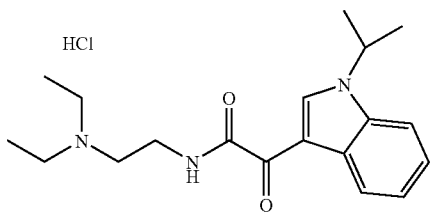

The title compound was prepared according to general procedure B described in Scheme 1 from N-isopropylindole and N,N-diethylethylenediamine (120 mg, 5% yield): $^1$H NMR (400 MHz, CDCl$_3$): δ 12.56 (NH$^+$, br s, 1H), 8.98 (s, 1H), 8.46 (dd, 1H), 8.39 (t, 1H), 7.44 (m, 1H), 7.35 (m, 2H), 4.72 (m, 1H), 3.96 (q, 2H), 3.20 (m, 6H), 1.62 (m, 6H), 1.47 (t, 6H); MS (ESI) m/z: Calculated for C$_{19}$H$_{27}$N$_3$O$_2$: 329.2. Found: 330.3 (M+H)$^+$.

Example 4

2-(1-Ethyl-1H-indol-3-yl)-2-oxo-N-(2-(piperidin-1-yl)ethyl)acetamide hydrochloride N-Ethylindole

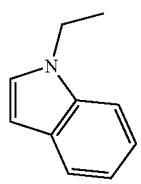

The title compound was prepared according to general procedure A described in Scheme 1 from indole and bromoethane. The crude material was used directly without further purification 2-(1-Ethyl-1H-indol-3-yl)-2-oxo-N-(2-(piperidin-1-yl)ethyl)acetamide hydrochloride

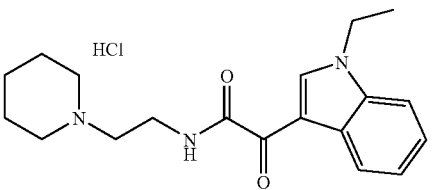

The title compound was prepared according to general procedure B described in Scheme 1 from N-ethylindole and 1-piperidimethylamine (170 mg, 47% yield): $^1$H NMR (400 MHz, CDCl$_3$): δ 8.88 (s, 1H), 8.44 (m, 1H), 8.39 (m, 1H), 7.40 (m, 1H), 7.29 (m, 2H), 4.24 (q, 2H), 4.00 (m, 2H), 3.61 (m, 2H), 3.18 (m, 2H), 2.71 (m, 2H), 2.37 (m, 2H), 1.87 (m, 3H), 1.54 (m, 4H); MS (ESI) m/z: Calculated for C$_{19}$H$_{25}$N$_3$O$_2$: 327.2. Found: 328.3 (M+H)$^+$.

Example 5

2-(1-sec-Butyl-1H-indol-3-yl)-2-oxo-N-(2-(piperidin-1-yl)ethyl)acetamide hydrochloride N-sec-Butyl-1H-indole

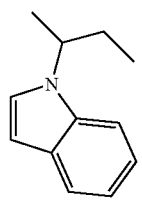

The title compound was prepared according to general procedure A described in Scheme 1 from indole and 2-bromobutane. The crude material was used directly without further purification.

2-(1-sec-Butyl-1H-indol-3-yl)-2-oxo-N-(2-(piperidin-1-yl)ethyl)acetamide hydrochloride

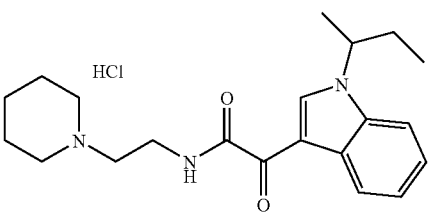

The title compound was prepared according to general procedure B described in Scheme 1 from N-sec-butylindole and 1-piperidimethylamine (193 mg, 25% yield): $^1$H NMR (400 MHz, CDCl$_3$): δ 12.47 (NH$^+$, br s, 1H), 8.93 (s, 1H), 8.45 (dd, 1H), 8.39 (t, 1H), 7.42 (m, 1H), 7.32 (m, 2H), 4.45 (m, 1H), 4.00 (q, 2H), 3.62 (d, 2H), 3.19 (q, 2H), 2.72 (q, 2H), 2.34 (q, 2H), 1.92 (m, 5H), 1.61 (d, 3H), 1.42 (m, 1H), 0.89 (t, 3H); MS (ESI) m/z: Calculated for C$_{21}$H$_{29}$N$_3$O$_2$: 355.2. Found: 356.3 (M+H)$^+$.

Example 6

2-(5-Chloro-1-isopropyl-1H-indol-3-yl)-2-oxo-N-(2-(piperidin-1-yl)ethyl)acetamide hydrochloride

5-Chloro-N-isopropyl-1H-indole

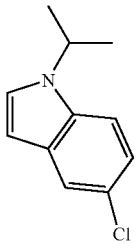

The title compound was prepared according to general procedure A described in Scheme 1 from 5-chloroindole and 2-iodopropane (650 mg, 65% yield).

2-(5-Chloro-1-isopropyl-1H-indol-3-yl)-2-oxo-N-(2-(piperidin-1-yl)ethyl)acetamide hydrochloride

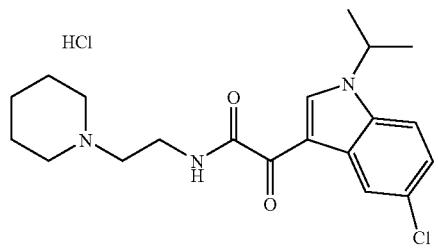

The title compound was prepared according to general procedure B described in Scheme 1 from 5-chloro-N-isopropylindole and 1-piperidimethylamine (500 mg, 60% yield): $^1$H NMR (400 MHz, DMSO-d$^6$): δ 10.36 (NH$^+$, br s 1H), 9.08 (t, 1H), 8.90 (s, 1H), 8.22 (d, 1H), 7.77 (d, 1H), 7.35 (dd, 1H), 4.88 (m, 1H), 3.63 (q, 2H), 3.47 (d, 2H), 3.19 (m, 2H), 2.89 (m, 2H), 1.77 (m, 4H), 1.48 (d, 6H), 1.26 (dd, 2H); MS (ESI) m/z: Calculated for C$_{20}$H$_{26}$ClN$_3$O$_2$: 375.2. Found: 376.2 (M+H)$^+$.

Example 7

2-(1-Isopropyl-6-nitro-1H-indol-3-yl)-2-oxo-N-(2-(piperidin-1-yl)ethyl)acetamide hydrochloride

1-Isopropyl-6-nitro-1H-indole

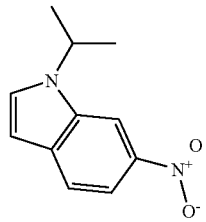

The title compound was prepared according to general procedure A described in Scheme 1 from indole and 2-bromobutane (1.60 g, 51% yield).

2-(1-Isopropyl-6-nitro-1H-indol-3-yl)-2-oxo-N-(2-(piperidin-1-yl)ethyl)acetamide hydrochloride

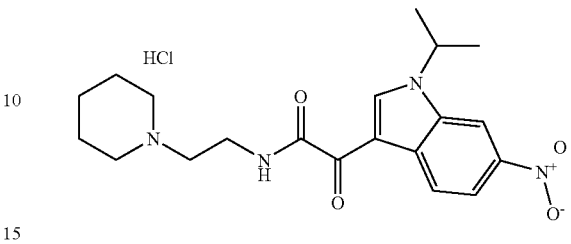

The title compound was prepared according to general procedure B described in Scheme 1 from 6-nitro-N-isopropylindole and 1-piperidimethylamine (600 mg, 84% yield): $^1$H NMR (400 MHz, CDCl$_3$): δ 9.32 (s, 1H), 8.55 (d, 1H), 8.40 (d, 1H), 8.22 (q, 1H), 7.93 (br s, 1H), 4.80 (m, 1H), 3.47 (q, 2H), 2.54 (t, 2H), 2.43 (br s, 4H), 1.66 (d, 6H), 1.61 (qi, 4H), 1.46 (d, 2H); MS (ESI) m/z: Calculated for C$_{20}$H$_{26}$N$_4$O$_4$: 386.2. Found: 387.2 (M+H)$^+$.

Example 8

2-(6-Amino-1-isopropyl-1H-indol-3-yl)-2-oxo-N-(2-(piperidin-1-yl)ethyl)acetamide hydrochloride

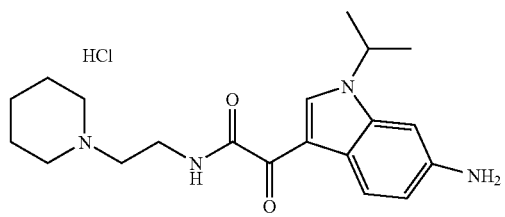

The title compound was prepared according to the following procedure: 2-(1-isopropyl-6-nitro-1H-indol-3-yl)-2-oxo-N-(2-(piperidin-1-yl)ethyl)acetamide (500 mg, 1.29 mmol) was dissolved in EtOAc. SnCl$_2$.2H$_2$O (1.39 g, 6.50 mmol) was added portionwise and the mixture was heated at reflux for 8 hr. The reaction mixture was then cooled and treated with sat. NaHCO$_3$. After stirring at RT for 30 min., the reaction mixture was extracted with EtOAc, dried over MgSO$_4$, concentrated down and then converted to the HCl salt to yield the title compound (350 mg, 76% yield): $^1$H NMR (400 MHz, DMSO-d$^6$): δ 10.30 (NH$_2$ and NH$^+$, br, s, 3H), 9.04 (s, 1H), 8.87 (s, 1H), 8.26 (s, 1H), 7.67 (s, 1H), 7.25 (s, 1H), 4.77 (m, 1H), 3.60 (m, 2H), 3.17 (m, 2H), 2.86 (m, 2H), 1.74 (m, 4H), 1.50 (d, 6H), 1.28 (m, 2H), 1.04 (m, 2H); MS (ESI) m/z: Calculated for C$_{20}$H$_{28}$N$_4$O$_2$: 356.2. Found: 357.2 (M+H)$^+$.

Example 9

2-(6-Amino-7-chloro-1-isopropyl-1H-indol-3-yl)-2-oxo-N-(2-(piperidin-1-yl)ethyl)acetamide hydrochloride

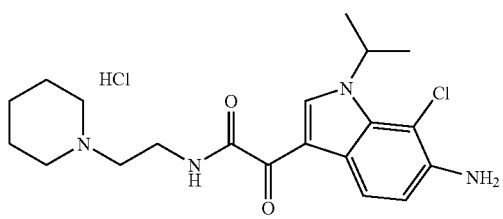

The title compound was prepared according to the following procedure: a solution of 2-(6-amino-1-isopropyl-1H-indol-3-yl)-2-oxo-N-(2-(piperidin-1-yl)ethyl)acetamide (150 mg, 0.42 mmol) and NCS (56 mg, 0.42 mmol) in DMF was stirred at RT overnight. The crude mixture was purified on silica gel (Biotage, 0-10% MeOH/DCM, 30 min.) to provide 2-(6-amino-7-chloro-1-isopropyl-1H-indol-3-yl)-2-oxo-N-(2-(piperidin-1-yl)ethyl)acetamide. This free amine was dissolved in DCM (2 mL) and 1M HCl in $Et_2O$ (2 mL) was added. The mixture was stirred at RT for 2 hr and additional 5 mL of $Et_2O$ was added. The light yellow solid was filtered and washed with $Et_2O$ to yield the title compound (32 mg, 18% yield): $^1$H NMR (400 MHz, DMSO-d$^6$): δ 10.10 (NH$^+$, br s, 1H), 9.04 (t, 1H), 8.79 (s, 1H), 8.07 (d, 1H), 7.09 (d, 1H), 5.56 (m, 1H), 4.18 (br s, $NH_2$), 3.61 (q, 2H), 3.48 (d, 2H), 3.19 (d, 2H), 2.87 (m, 2H), 1.76 (m, 4H), 1.68 (d, 1H), 1.51 (d, 6H), 1.37 (m, 1H); MS (ESI) m/z: Calculated for $C_{20}H_{27}ClN_4O_2$: 390.2. Found: 391.2 (M+H)$^+$.

Example 10

2-(1-Isopropyl-1H-indol-3-yl)-2-oxo-N-(2-(pyrrolidin-1-yl)ethyl)acetamide

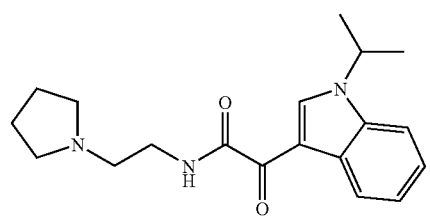

The title compound was prepared according to general procedure B described in Scheme 1 from N-isopropylindole and 1-pyrrolidimethylamine (106 mg, 11% yield): $^1$H NMR (400 MHz, CDCl$_3$): δ 9.13 (s, 1H), 8.46 (m, 1H), 7.93 (br s, 1H), 7.44 (m, 1H), 7.37-7.24 (m, 2H), 4.72 (m, 1H), 3.50 (m, 2H), 2.70 (t, 2H), 2.57 (m, 4H), 1.83-1.78 (m, 4H), 1.62 (d, 6H); MS (ESI) m/z: Calculated for $C_{19}H_{25}N_3O_2$: 327.2. Found: 328.3 (M+H)$^+$.

Example 11

2-(1-Isopropyl-5-methoxy-1H-indol-3-yl)-2-oxo-N-(2-(piperidin-1-yl)ethyl)acetamide

5-Methoxy-N-isopropylindole

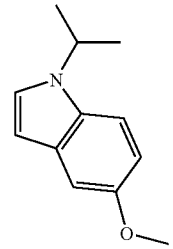

The title compound was prepared according to general procedure A described in Scheme 1 from 5-methoxyindole and 2-iodopropane (640 mg, 22% yield).

2-(1-Isopropyl-5-methoxy-1H-indol-3-yl)-2-oxo-N-(2-(piperidin-1-yl)ethyl)acetamide

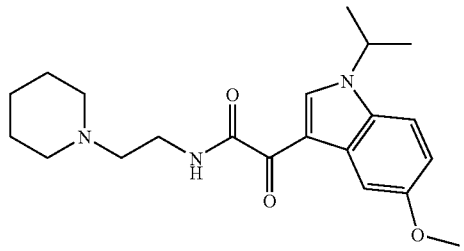

The title compound was prepared according to general procedure B described in Scheme 1 from 5-methoxy-N-isopropylindole and 1-piperidimethylamine (103 mg, 28% yield): $^1$H NMR (400 MHz, CDCl$_3$): δ 9.06 (s, 1H), 7.97 (d, 1H), 7.93 (m, 1H), 7.32 (d, 1H), 6.96 (m, 1H), 4.65 (m, 1H), 3.92 (s, 3H), 3.47 (q, 2H), 2.54 (t, 2H), 2.43 (br s, 4H), 1.63 (m, 4H), 1.61 (d, 6H), 1.45 (m, 2H); MS (ESI) m/z: Calculated for $C_{21}H_{29}N_3O_3$: 371.2. Found: 372.3 (M+H)$^+$.

Example 12

2-(1-Isopropyl-5-methyl-1H-indol-3-yl)-2-oxo-N-(2-(piperidin-1-yl)ethyl)acetamide 1-Isopropyl-5-methyl-1H-indole

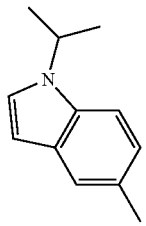

The title compound was prepared according to general procedure A described in Scheme 1 from 5-methylindole and 2-iodopropane (500 mg, 29% yield).

2-(1-isopropyl-5-methyl-1H-indol-3-yl)-2-oxo-N-(2-(piperidin-1-yl)ethyl)acetamide

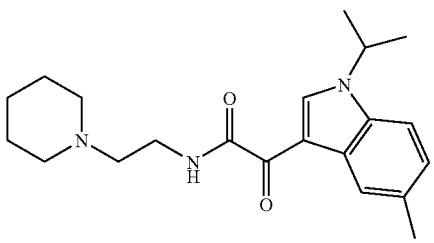

The title compound was prepared according to general procedure B described in Scheme 1 from 5-methyl-N-isopropylindole and 1-piperidimethylamine (106 mg, 30% yield): $^1$H NMR (400 MHz, CDCl$_3$): δ 9.08 (s, 1H), 8.28 (t, 1H), 7.96 (br s, 1H), 7.32 (d, 1H), 7.15 (d, 1H), 4.07 (m, 1H), 3.47 (q, 2H), 2.54 (t, 2H), 2.51 (s, 3H), 2.43 (m, 2H), 1.62 (m, 6H), 1.60 (d, 6H), 1.47 (m, 2H); MS (ESI) m/z: Calculated for C$_{21}$H$_{29}$N$_3$O$_2$: 355.2. Found: 356.3 (M+H)$^+$.

Example 13

N-(1-(3-Hydroxypropyl)piperidin-4-yl)-2-(1-isopropyl-1H-indol-3-yl)-2-oxoacetamide

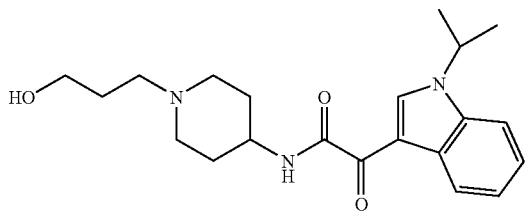

The title compound was prepared according to general procedure B described in Scheme 1 from N-isopropylindole (2.1 g, 13.4 mmol) and 3-(4-aminopiperidin-1-yl)propan-1-ol (3.7 g, 16 mmol) to obtain the title compound in 10% yield, 510 mg: $^1$H NMR (400 MHz, CDCl$_3$): δ 9.13 (s, 1H), 8.44 (m, 1H), 7.52 (d, 1H), 7.44 (m, 1H), 7.34 (m, 2H), 4.72 (m, 1H), 3.87 (br s, 11-1), 3.82 (t, 2H), 3.02 (br m, 2H), 2.65 (t, 2H), 2.22 (br m, 2H), 2.03 (d, 2H), 1.76 (m, 2H), 1.62 (d and m, 9H); MS (ESI) m/z: Calculated for C$_{21}$H$_{29}$N$_3$O$_3$: 371.2. Found: 372.3 (M+H)$^+$.

Example 14

2-(1-Isopropyl-1H-indol-3-yl)-2-oxo-N-(1-propylpiperidin-4-yl)acetamide

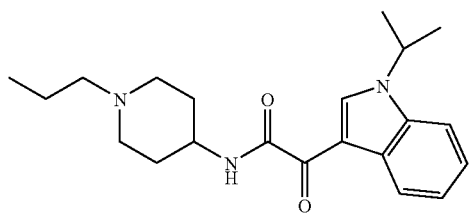

The title compound was prepared according to general procedure B described in Scheme 1 from N-isopropylindole and 1-propyl-4-piperidineamine (75.0 mg, 47% yield): $^1$H NMR (400 MHz, CDCl$_3$): δ 9.14 (s, 1H), 8.45-8.43 (m, 1H), 7.52 (d, 1H), 7.45-7.43 (m, 1H), 7.35 (m, 2H), 4.71 (m, 1H), 3.89-3.85 (m, 1H), 2.94 (d, 2H), 2.34 (m, 2H), 2.20 (t, 2H), 2.02 (d, 2H), 1.74-1.64 (m, 2H), 1.62 (d, 6H), 1.58-1.53 (m, 2H), 0.92 (t, 3H); MS (ESI) m/z: Calculated for C$_{21}$H$_{29}$N$_3$O$_2$: 355.2. Found: 356.3 (M+H)$^+$.

Example 15

N-((1-Isobutylpiperidin-4-yl)methyl)-2-(1-isopropyl-1H-indol-3-yl)-2-oxoacetamide

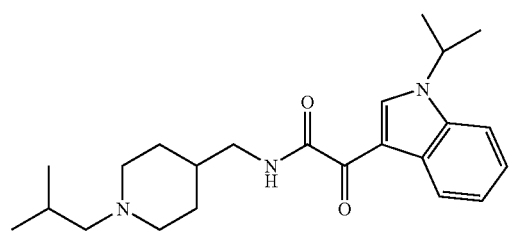

The title compound was prepared according to general procedure B described in Scheme 1 from N-isopropylindole and (1-isobutylpiperidin-4-yl)methanamine (140.0 mg, 37% yield): $^1$H NMR (400 MHz, CDCl$_3$): δ 9.15 (s, 1H), 8.44 (m, 1H), 7.69 (t, 1H), 7.43 (m, 1H) 7.39 (m, 2H), 4.70 (m, 1H), 3.27 (t, 2H), 2.86 (d, 2H), 2.04 (d, 2H), 1.85 (t, 2H), 1.75 (m, 4H), 1.61 (d, 6H), 1.34 (q, 2H), 0.88 (d, 6H), MS (ESI) m/z: Calculated for C$_{23}$H$_{33}$N$_3$O$_2$: 383.3. Found: 384.3 (M+H)$^+$.

Example 16

2-(1-Isopropyl-1H-indol-3-yl)-2-oxo-N-(2-(4-(trifluoromethyl)piperidin-1-yl)ethyl)acetamide

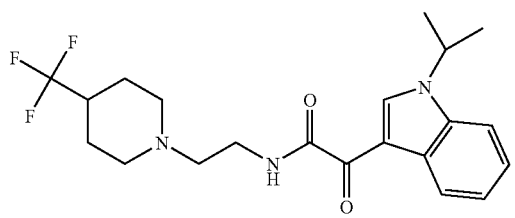

The title compound was prepared according to general procedure B described in Scheme 1 from N-isopropylindole and 2-(4-(trifluoromethyl)piperidin-1-yl)ethanamine (180 mg, 44% yield): $^1$H NMR (400 MHz, CDCl$_3$): δ 9.11 (s, 1H), 8.45 (m, 1H), 7.88 (br t, 1H), 7.44 (m, 1H), 7.31 (m, 2H), 4.71 (m, 1H), 3.48 (q, 2H), 3.02 (d, 2H), 2.58 (t, 2H), 2.02 (t, 3H), 1.85 (d, 2H), 1.67 (t, 2H), 1.61 (d, 6H); MS (ESI) m/z: Calculated for C$_{21}$H$_{26}$F$_3$N$_3$O$_2$: 409.2. Found: 410.1 (M+H)$^+$.

Example 17

2-(1-Isopropyl-1H-pyrrolo[2,3-b]pyridin-3-yl)-2-oxo-N-(2-(piperidin-1-yl)ethyl)acetamide N-Isopropyl-7-azaindole

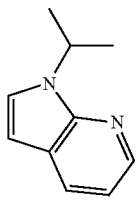

The title compound was prepared according to general procedures described in Scheme 1 from 7-azaindole and isopropyl iodide (949 mg, 70% yield): $^1$H NMR (300 MHz, CDCl$_3$) δ 8.31 (dd, 1H), 7.90 (dd, 1H), 7.32 (d, 1H), 7.04 (dd, 1H), 6.47 (d, 1H), 5.22 (m, 1H), 1.52 (d, 6H).

2-(1-Isopropyl-1H-pyrrolo[2,3-b]pyridin-3-yl)-2-oxo-N-(2-(piperidin-1-yl)ethyl)acetamide

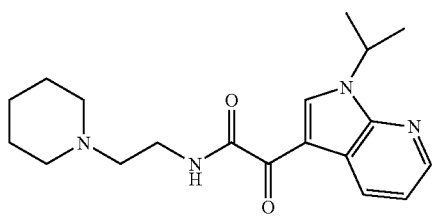

The title compound was prepared according to general procedure B described in Scheme 1 from N-isopropyl-7-azaindole and 1-piperidimethylamine (220 mg, 76% yield): $^1$H NMR (300 MHz, CDCl$_3$) δ 9.14 (s, 1H), 8.60 (dd, 1H), 8.35 (dd, 1H), 7.75 (br, 1H, NH), 7.21 (dd, 1H), 5.17 (m, 1H), 3.42 (q, 2H), 2.49 (t, 2H), 2.38 (br t, 4H), 1.55 (d and m, 6H+4H) 1.40 (m, 2H); MS (ESI) m/z: Calculated for C$_{19}$H$_{26}$N$_4$O$_2$: 342.2. Found: 343.8 (M+H)$^+$.

Example 18

2-(1-Isopropyl-1H-indol-3-yl)-2-oxo-N-(2-(4-propylpiperidin-1-yl)ethyl)acetamide TFA salt

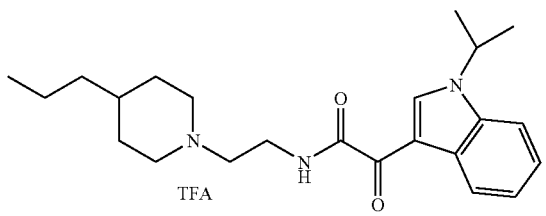

The title compound was prepared according to general procedures described in Schemes 1 and 3 from 4-propylpiperidine and N-isopropylindole (7 mg): $^1$H NMR (400 MHz, CDCl$_3$): δ 9.11 (s, 1H), 8.45 (d, 1H), 7.95 (s, 1H), 7.43 (m, 1H), 7.34 (m, 2H), 4.71 (m, 1H), 3.50 (q, 2H), 2.96 (d, 2H), 2.60 (m, 2H), 2.04 (t, 2H), 1.68 (d, 2H), 1.61 (d, 6H), 1.28 (m, 7H), 0.89 (t, 3H); MS (ESI) m/z: Calculated for C$_{23}$H$_{33}$N$_3$O$_2$: 383.3. Found: 384.4 (M+H)$^+$.

Example 19

N-(1-Butylpiperidin-4-yl)-2-(1-isopropyl-1H-indol-3-yl)-2-oxoacetamide tert-Butyl 4-(2-(1-isopropyl-1H-indol-3-yl)-2-oxoacetamido)piperidine-1-carboxylate

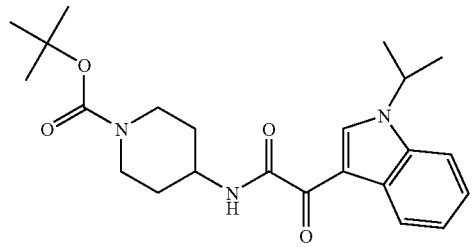

The title compound was prepared according to general procedure C described in Scheme 2. N-Isopropylindole (1 g, 6 mmol) was treated with ether (10 mL), cooled to 0° C. and treated dropwise with oxalyl chloride (0.62 mL, 7 mmol). The reaction was gradually warmed to RT over a 3 h period affording a yellow precipitate. The reaction mixture was concentrated under reduced pressure and the resulting yellow solid was dissolved in DCM (20 mL) cooled to 0° C. and treated with a solution of tert-butyl 4-aminopiperidine-1-carboxylate (1.5 g, 7 mmol) and triethylamine (5.2 mL, 38 mmol) in DCM (10 mL). The reaction mixture was allowed to warm to RT and stirred for 14 h. The reaction mixture was concentrated under reduced pressure and the crude material was purified on silica gel (Biotage, 15-50% EtOAc/Hexanes, 30 min.) to provide the title compound as a yellow oil (1.3 g, 50% yield).

2-(1-Isopropyl-1H-indol-3-yl)-2-oxo-N-(piperidin-4-yl)acetamide hydrochloride

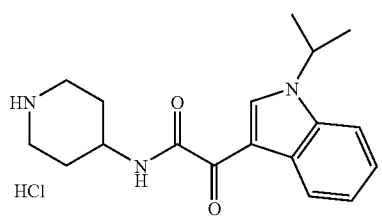

The title compound was prepared according to general procedure D described in Scheme 2. tert-Butyl 4-(3-(1-isopropyl-1H-indol-3-yl)-2,3-dioxopropyl)piperidine-1-carboxylate (1.3 g, 3 mmol) was treated with 3 N HCl in MeOH (5.1 mL, 15 mmol) and stirred at RT for 30 min The reaction mixture was concentrated under reduced pressure to afford the title compound as a pink solid (0.960 g, 99% yield).

N-(1-Butylpiperidin-4-yl)-2-(1-isopropyl-1H-indol-3-yl)-2-oxoacetamide

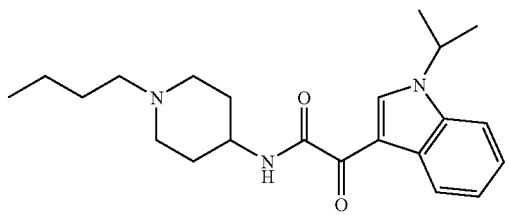

The title compound was prepared according to general procedure E described in Scheme 2. 2-(1-Isopropyl-1H-indol-3-yl)-2-oxo-N-(piperidin-4-yl)acetamide hydrochloride (200 mg, 0.64 mmol) was treated with acetonitrile (3 mL), $K_2CO_3$ (265 mg, 1.91 mmol), and n-butyl bromide (175 mg, 1.28 mmol). The reaction mixture was stirred at 65° C. for 72 h and was then concentrated under reduced pressure. The crude material was purified on silica gel (Biotage, 2-10% MeOH/DCM, 30 min.) to provide the title compound as a pink solid (68 mg, 29% yield): $^1$H NMR (400 MHz, CDCl$_3$): δ 9.11 (s, 1H), 8.43 (t, 1H), 7.56 (d, 1H), 7.43 (q, 1H), 7.35 (t, 2H), 4.71 (m, 1H), 3.90 (m, 1H), 3.03 (d, 2H), 2.48 (d, 2H), 2.31 (t, 2H), 2.05 (d, 2H), 1.80 (m, 2H), 1.61 (d+m, 8H), 1.34 (m, 2H), 0.94 (t, 3H);

MS (ESI) m/z: Calculated for $C_{22}H_{31}N_3O_2$: 369.2. Found: 370.3 (M+H)$^+$.

Example 20

2-(1-Isopropyl-1H-indol-3-yl)-N-(1-(3-methoxypropyl)piperidin-4-yl)-2-oxoacetamide TFA salt

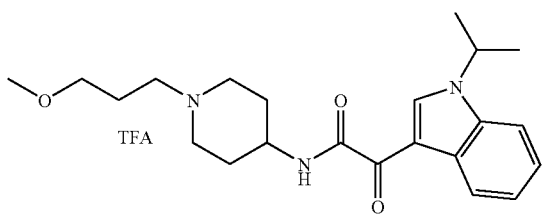

The title compound was prepared according to general procedures C, D and E described in Scheme 2 from N-isopropylindole and 1-bromo-3-methoxypropane (41 mg, 13%): $^1$H NMR (400 MHz, CDCl$_3$): δ 9.01 (s, 1H), 8.43 (m, 1H), 7.70 (m, 1H), 7.43 (m, 1H), 7.36 (m, 2H), 4.72 (m, 1H), 4.05 (m, 1H), 3.81 (d, 2H), 3.47 (t, 2H), 3.32 (s, 3H), 3.18 (m, 2H), 2.78 (t, 2H), 2.04 (m, 6H), 1.62 (d, 6H); MS (ESI) m/z: Calculated for $C_{22}H_{31}N_3O_3$: 385.2. Found: 386.4 (M+H)$^+$.

Example 21

2-(1-Isopropyl-1H-indol-3-yl)-N-(1-(2-(methylsulfonamido)ethyl)piperidin-4-yl)-2-oxoacetamide TFA salt tert-Butyl 2-(4-(2-(1-isopropyl-1H-indol-3-yl)-2-oxoacetamido)piperidin-1-yl)ethylcarbamate

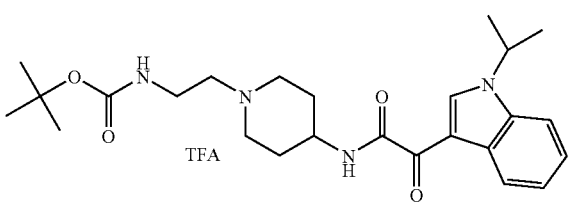

The title compound was prepared according to general procedure C described in Scheme 2. 2-(1-Isopropyl-1H-indol-3-yl)-2-oxo-N-(piperidin-4-yl)acetamide hydrochloride (200 mg, 0.64 mmol) was treated with acetonitrile (3 mL), $K_2CO_3$ (265 mg, 1.91 mmol), and tert-butyl 2-bromoethylcarbamate (266 mg, 1.28 mmol). The reaction mixture was stirred at 65° C. for 72 h and was then concentrated under reduced pressure. The crude material was purified by silica chromatography (Biotage, 0-5% MeOH/DCM, 30 min.) to provide the title compound as a brown oil. The material was further purified using reverse phase HPLC to provide the desired product as a pink solid TFA salt (132 mg, 45%).

N-(1-(2-Aminoethyl)piperidin-4-yl)-2-(1-isopropyl-1H-indol-3-yl)-2-oxoacetamide hydrochloride The title compound was prepared according to general procedure D described in Scheme 2. tert-Butyl 2-(4-(2-(1-isopropyl-1H-indol-3-yl)-2-oxoacetamido)piperidin-1-yl) ethylcarbamate (132 mg, 0.29 mmol) was treated with 3 N HCl in MeOH (2 mL, 1.2 mmol) and stirred at RT for 30 min. The reaction mixture was concentrated under reduced pressure to afford the title compound as a pink solid (106 mg, 100%), which was used without further purification in the sulfonamide formation.

2-(1-Isopropyl-1H-indol-3-yl)-N-(1-(2-(methylsulfonamido)ethyl)piperidin-4-yl)-2-oxoacetamide TFA salt

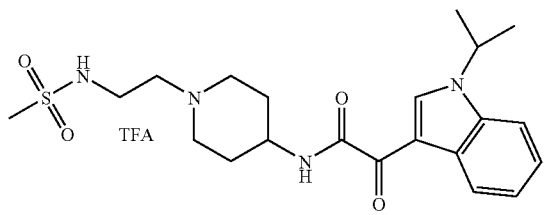

The title compound was prepared according to general procedure D described in Scheme 2. N-(1-(2-Aminoethyl)piperidin-4-yl)-2-(1-isopropyl-1H-indol-3-yl)-2-oxoacetamide hydrochloride (106 mg, 0.30 mmol) was treated with DCM (2 mL) and triethylamine (120 µL, 0.9 mmol). The reaction mixture was cooled to 0° C. and treated dropwise with methanesulfonyl chloride (41 mg, 0.36 mmol) gradually warmed to RT and stirred for 14 h. The crude reaction mixture was diluted with DCM (2 mL) and washed with $H_2O$ (1×3 mL). The organic layer was dried over anhydrous $Na_2SO_4$ and concentrated under reduced pressure. The crude material was purified by silica chromatography (Biotage, 0-6% MeOH/DCM, 30 min.) to provide the title compound as a yellow oil. The material was further purified using reverse phase HPLC to provide the desired product as a pink solid TFA salt (59 mg, 36%): $^1$H NMR (400 MHz, $CDCl_3$): δ 9.01 (s, 1H), 8.40 (t, 1H), 7.78 (br s, 1H), 7.43 (t, 1H), 7.35 (t, 2H), 4.71 (m, 1H), 4.05 (m, 1H), 3.80 (m, 2H), 3.57 (m, 2H), 3.31 (m, 2H), 2.99 (s, 3H), 2.90 (m, 2H), 2.21-2.12 (m, 4H), 1.61 (d, 6H), 0.92-0.90 (m, 1H); MS (ESI) m/z: Calculated for $C_{21}H_{30}N_4O_4S$: 434.2. Found: 435.4 $(M+H)^+$.

Example 22

N-(2-(4-(2-Hydroxyethyl)piperidin-1-yl)ethyl)-2-(1-isopropyl-1H-indol-3-yl)-2-oxoacetamide hydrochloride

2-(4-(2-Hydroxyethyl)piperidin-1-yl)acetonitrile

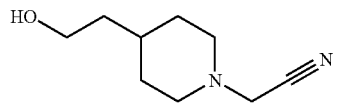

The title compound was prepared according to general procedure G described in Scheme 3. 2-(Piperidin-4-yl)ethanol (1.2 g, 9.3 mmol) was treated with 2-chloroacetonitrile (1.4 g, 18.6 mmol), triethylamine (10.4 mL, 74.3 mmol) and stirred at RT for 14 h. The crude reaction mixture was diluted with $Et_2O$ (25 mL) and washed with $H_2O$ (3×10 mL). The organic layer was dried over $Na_2SO_4$ and concentrated under reduced pressure to afford the title compound as a yellow oil (1.56 g, 100%), which was used without further purification.

2-(1-(2-Aminoethyl)piperidin-4-yl)ethanol hydrochloride

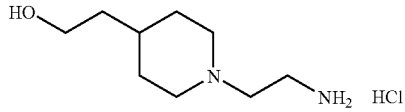

The title compound was prepared according to general procedure H described in Scheme 3. 2-(4-(2-Hydroxyethyl)piperidin-1-yl)acetonitrile (1.2 g, 7.13 mmol) was dissolved in ether (5 mL) and added carefully to a slurry of $LiAlH_4$ (8.3 equiv., 2.25 g, 59 mmol) in ether (25 mL) and stirred at RT under Ar for 14 h. The crude reaction mixture containing a white precipitate was cooled to 0° C. and treated dropwise with 10% aqueous NaOH (4 mL) and stirred for 30 min. The cooled mixture was treated with $H_2O$ (8.1 mL) to provide a thick precipitate. The mixture was then treated with ether (20 mL), stirred and filtered. The filter cake was washed with ether (5×20 mL). The combined ether layer was concentrated under reduced pressure to provide a concentrated solution in ether/$H_2O$ that was acidified to pH 2 with 1 N HCl. The mixture was concentrated under reduced pressure to provide the title compound as a dark yellow oil (923 mg, 62%).

N-(2-(4-(2-Hydroxyethyl)piperidin-1-yl)ethyl)-2-(1-isopropyl-1H-indol-3-yl)-2-oxoacetamide hydrochloride

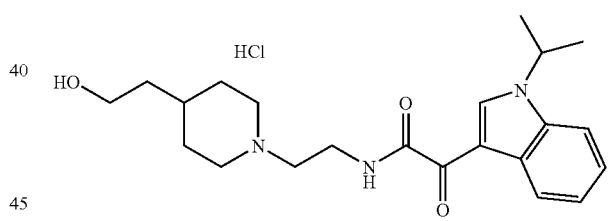

The title compound was prepared according to general procedure B described in Scheme 1. N-Isopropylindole (150 mg, 0.94 mmol) was converted to 2-(1-isopropyl-1H-indol-3-yl)-2-oxoacetyl chloride as described in example 1 and treated with a solution of 2-(1-(2-aminoethyl)piperidin-4-yl)ethanol (236 mg, 1.13 mmol), triethylamine (1.3 mL, 9.4 mmol) in DCM (2 mL) and stirred at RT for 14 h. The reaction mixture was then washed with sat. $NaHCO_3$ (1×3 mL), $H_2O$ (1×3 mL), dried over $Na_2SO_4$ and concentrated under reduced pressure. The crude material was purified by silica chromatography (Biotage, 10-50% MeOH/DCM, 30 min.) to provide N-(2-(4-(2-hydroxyethyl)piperidin-1-yl)ethyl)-2-(1-isopropyl-1H-indol-3-yl)-2-oxoacetamide and further purified using reverse phase HPLC. The purified material was converted to the HCl salt to afford (27 mg, 7% yield): $^1$H NMR (400 MHz, $CDCl_3$): δ 9.11 (s, 1H), 8.45 (m, 1H), 7.93 (t, 1H), 7.44 (m, 1H), 7.34 (m, 2H), 4.71 (m, 1H), 3.71 (t, 2H), 3.47 (q, 2H), 2.92 (d, 2H) 2.55 (t, 2H), 2.01 (t, 2H), 1.70 (d, 2H), 1.62 (d, 6H), 1.53 (q, 3H), 1.33 (t, 3H); MS (ESI) m/z: Calculated for $C_{22}H_{31}N_3O_3$: 385.2. Found: 385.5 $(M+H)^+$.

Example 23

N-(2-(4-ethylpiperidin-1-yl)ethyl)-2-(1-isopropyl-1H-indol-3-yl)-2-oxoacetamide hydrochloride

4-Ethylpiperidine

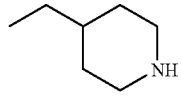

The title compound was prepared according to general procedure F described in Scheme 3. 4-Ethylpyridine (400 mg, 3.73 mmol) was treated with triethylsilane (12 mL, 75 mmol), PdOH (20 wt. % Pd on activated carbon, 80 mg) and acetic acid (cat. 2 drops) in a 40 mL vial. Gas evolution immediately started and the vial was capped until there was no visible gas evolution (~30 min.). The reaction mixture was then heated at 50° C. for 14 h with shaking. LCMS show clean conversion to the title compound, it was used directly without further purification.

2-(4-Ethyl-piperidin-1-yl)acetonitrile

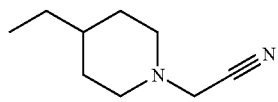

The title compound was prepared according to general procedure G described in Scheme 3 from 4-ethylpiperidine and 2-chloroacetonitrile. The crude solution was used directly without further purification.

2-(4-Ethylpiperidin-1-yl)ethanamine hydrochloride

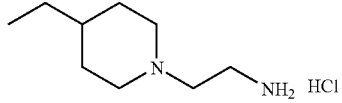

The title compound was prepared according to general procedure H described in Scheme 3. The crude triethylsilane solution of 2-(4-ethylpiperidin-1-yl)acetonitrile was added carefully to a slurry of LiAlH$_4$ (8.3 equiv., 1.2 g, 31 mmol) in ether (5 mL) and stirred at RT under Ar for 14 h. The crude reaction mixture containing a white precipitate was cooled to 0° C. and treated dropwise with 10% aqueous NaOH (1 mL) and stirred for 30 min. The cooled mixture was treated with H$_2$O (2.1 mL) to provide a thick precipitate. The mixture was then treated with ether (10 mL), stirred and filtered. The filter cake was washed with ether (5×10 mL). The combined ether layer was concentrated under reduced pressure to provide a concentrated solution in ether/H$_2$O that was acidified to pH 2 with 1 N HCl. The mixture was concentrated under reduced pressure to provide 2-(4-ethylpiperidin-1-yl)ethanamine hydrochloride as a brown oil (200 mg, 28% yield).

N-(2-(4-Ethylpiperidin-1-yl)ethyl)-2-(1-isopropyl-1H-indol-3-yl)-2-oxoacetamide hydrochloride

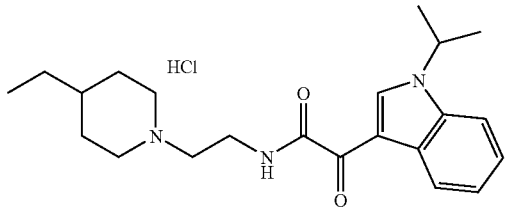

The title compound was prepared according to general procedure B described in scheme 1 from N-isopropylindole and 2-(4-ethylpiperidin-1-yl)ethanamine hydrochloride (56 mg, 15% yield): $^1$H NMR (400 MHz, CDCl$_3$): δ 9.12 (s, 1H), 8.45 (m, 1H), 7.92 (t, 1H), 7.43 (m, 1H), 7.33 (m, 2H), 4.71 (m, 1H), 3.47 (q, 2H), 2.92 (d, 2H), 2.55 (t, 2H), 1.99 (t, 2H), 1.67 (d, 2H), 1.61 (d, 6H), 1.24 (m, 5H), 0.80 (t, 3H); MS (ESI) m/z: Calculated for C$_{22}$H$_{31}$N$_3$O$_2$: 369.2. Found: 369.5 (M+H)$^+$.

Example 24

N-(2-(4-Butylpiperidin-1-yl)ethyl)-2-(1-isopropyl-1H-indol-3-yl)-2-oxoacetamide The title compound was prepared according to the procedure outlined in Scheme 4.

tert-Butyl-4-butyl-4-hydroxypiperidine-1-carboxylate

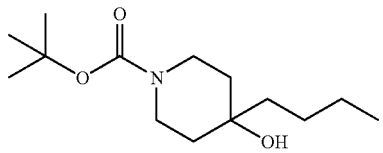

To a solution of n-butyl lithium (16.06 mL, 40.2 mmol, 2.5 M in hexanes) at −78° C., was drop-wise added a solution of N-Boc-4-piperidone (4.0 g, 20.1 mmol) in ether (10 mL). The resulting solution was allowed to warm to room temperature and stirred for one additional hour. The solution was cooled to 0° C. before being quenched by the drop-wise addition of saturated aqueous ammonium chloride (30 mL), and extracted with ethyl acetate (2×30 mL). The combined organic layer was then dried over sodium sulfate, filtered, and concentrated in vacuo to give the crude product as a yellow oil, which was then purified by silica chromatography on a Biotage (0-50% of EtOAc/Hexanes) to give the title compound as a colorless oil (1.66 g, still contaminated with the starting material ketone). This mixture was used in the next step without further purification.

tert-Butyl 4-butyl-5,6-dihydropyridine-1(2H)-carboxylate and tert-butyl 4-butylidenepiperidine-1-carboxylate

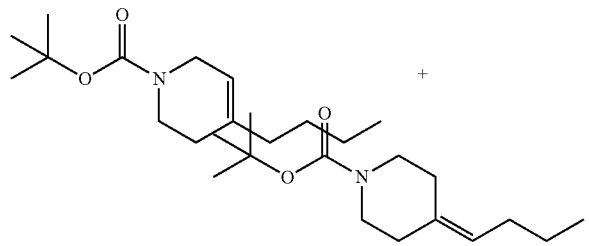

To a solution of tert-butyl-4-butyl-4-hydroxypiperidine-1-carboxylate (1.66 g, 6.44 mmol) in DCM (10 mL) at 0° C. was added triethyl amine (2.69 mL, 19.32 mmol) followed by the addition of methane sulfonic anhydride (2.69 g, 15.45 mmol) The reaction was allowed to warm to room temperature and stirred for 2 additional hours before being washed with saturated aqueous sodium bicarbonate (2×30 mL), dried over sodium sulfate, filtered, and concentrated in vacuo to give a yellow oil, which was then purified by silica chromatography on a Biotage (10%-20% EtOAc/Hexanes) to give a mixture of alkene products as a colorless oil (364 mg, 24% yield)

2-(4-Butylpiperidin-1-yl)ethanamine

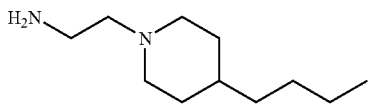

A mixture of tert-butyl 4-butyl-5,6-dihydropyridine-1 (2H)-carboxylate and tert-butyl 4-butylidenepiperidine-1-carboxylate (310 mg, 1.3 mmol) and methanolic HCl (1.73 mL, 3 N in MeOH) was stirred at room temperature for 1.5 hours. The mixture was concentrated in vacuo and used in the next step without any further purification.

To the crude amine salts was added chloroacetonitrile (0.15 mL, 2.3 mmol), triethylamine (0.64 mL, 4.6 mmol), and dichloromethane (4 mL). The mixture was stirred at room temperature for 16 hours, diluted with dichloromethane (10 mL), washed with water (3×10 mL), dried over sodium sulfate, filtered, and concentrated in vacuo to give a brown oil (160 mg) which was used in the next step without further purification.

The brown oil was dissolved in acetic acid (2 mL). Palladium on carbon (30 mg, 10% wt) was added and the mixture was stirred under a hydrogen balloon at room temperature for 2 days. Analysis by LC/MS showed formation of product along with remaining starting material. This crude mixture was filtered through a pad of celite and washed with additional ethyl acetate (20 mL) The filtrate was concentrated in vacuo to yield a yellow gum (150 mgs) which was used in the next step without further purification.

N-(2-(4-butylpiperidin-1-yl)ethyl)-2-(1-isopropyl-1H-indol-3-yl)-2-oxoacetamide

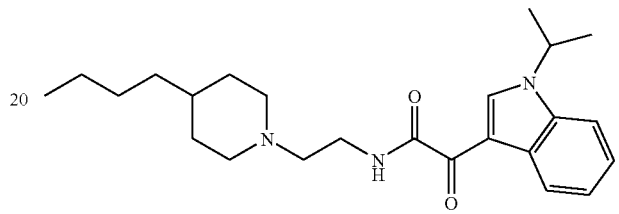

To a solution of N-isopropyl indole (100 mg, 0.63 mmol) in diethyl ether (2 mL) at 0° C. was drop-wise added oxalyl chloride (60 mL, 0.73 mmol). The mixture was allowed to warm to room temperature over a period of three hours and then concentrated in vacuo to give a yellow solid. To the yellow solid was added dichloromethane (2 mL), triethyl amine (0.525 mL, 3.77 mmol), and a solution of the crude 2-(4-butylpiperidin-1-yl)ethanamine (150 mg) in triethyl amine (0.525 mL, 3.77 mmol) and dichloromethane (1 mL). The mixture was stirred at room temperature for 66 hours, then washed with saturated aqueous sodium bicarbonate (1×5 mL) and water (1×5 mL), dried over sodium sulfate, filtered, and concentrated in vacuo to give a yellow oil, which was purified by silica chromatography on a Biotage (2-10% MeOH/CH$_2$Cl$_2$) to give a yellow gum (6 mg, 2% yield): $^1$H NMR (400 MHz, CDCl$_3$): δ 9.11 (s, 1H), 8.46 (m, 1H), 7.92 (t, 1H), 7.43 (m, 1H), 7.33 (m, 2H) 4.71 (m, 1H), 3.47 (q, 2H), 2.45 (d, 2H), 2.54 (t, 2H), 1.98 (t, 2H), 1.65 (m, 2H), 1.61 (d, 6H), 1.25 (m, 9H), 0.89 (t, 3H); MS (ESI) m/z: Calculated for C$_{24}$H$_{35}$N$_3$O$_2$: 397.3. Found: 398.3 (M+H)$^+$.

TABLE 1

| EXAMPLE COMPOUNDS | | | | |
|---|---|---|---|---|
| Example No. | Structure | m/z | Calc MW | Synthetic Methods |
| 1 | | 356.3 | 355.2 | Scheme 1 |

TABLE 1-continued

EXAMPLE COMPOUNDS

| Example No. | Structure | m/z | Calc MW | Synthetic Methods |
|---|---|---|---|---|
| 2 | 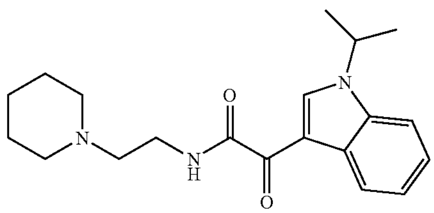 | 341.2 | 342.3 | Scheme 1 |
| 3 | 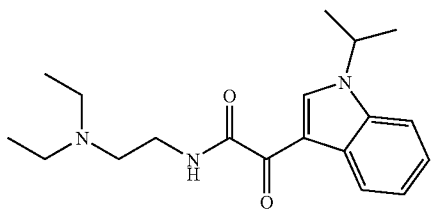 | 330.3 | 329.2 | Scheme 1 |
| 4 | 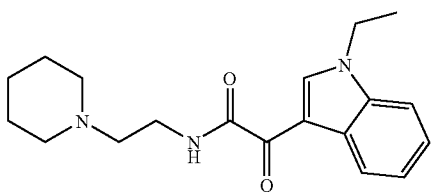 | 328.3 | 327.2 | Scheme 1 |
| 5 | 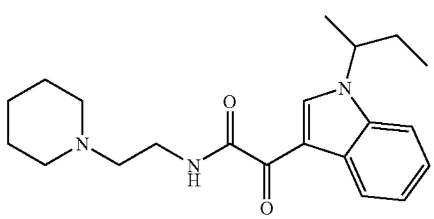 | 356.3 | 355.2 | Scheme 1 |
| 6 | 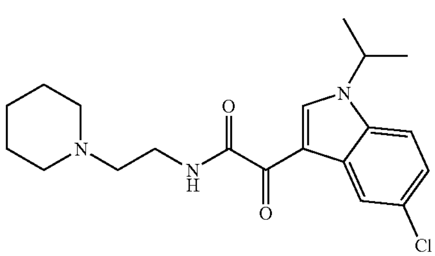 | 376.2 | 375.2 | Scheme 1 |
| 7 | 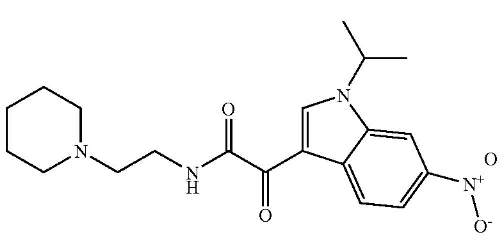 | 387.2 | 386.2 | Scheme 1 |

TABLE 1-continued
EXAMPLE COMPOUNDS
| Example No. | Structure | m/z | Calc MW | Synthetic Methods |
|---|---|---|---|---|
| 8 | 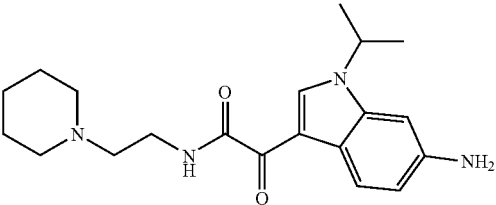 | 357.2 | 356.2 | Scheme 1 |
| 9 | 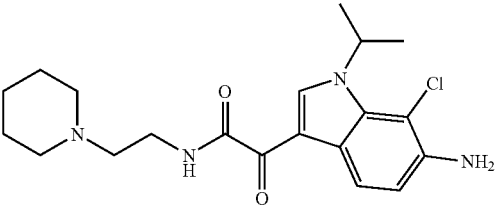 | 364.2 | 363.1 | Scheme 1 |
| 10 | 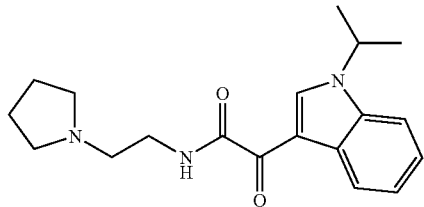 | 328.3 | 327.2 | Scheme 1 |
| 11 | 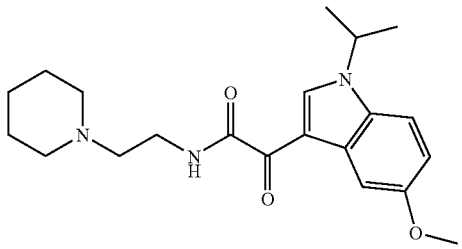 | 372.3 | 371.2 | Scheme 1 |
| 12 | 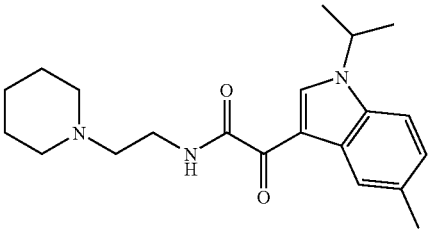 | 356.3 | 355.2 | Scheme 1 |
| 13 | 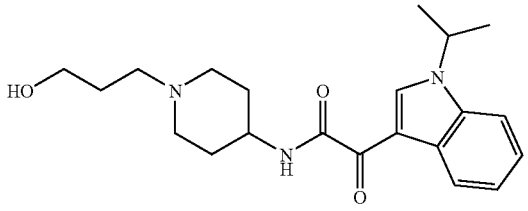 | 372.3 | 371.2 | Scheme 1 |

TABLE 1-continued

EXAMPLE COMPOUNDS

| Example No. | Structure | m/z | Calc MW | Synthetic Methods |
|---|---|---|---|---|
| 14 | 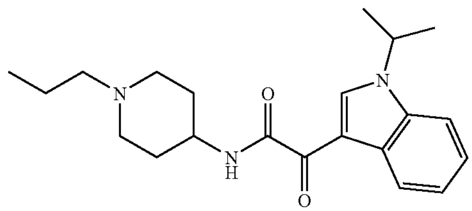 | 356.3 | 355.2 | Scheme 1 |
| 15 | 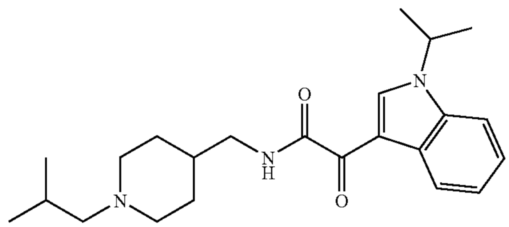 | 384.3 | 383.3 | Scheme 1 |
| 16 | 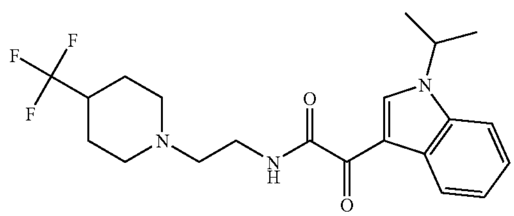 | 410.1 | 409.2 | Scheme 1 |
| 17 | 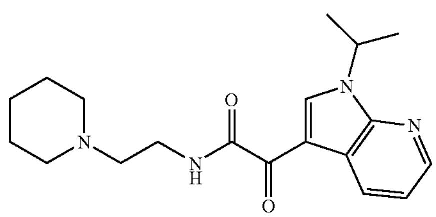 | 343.8 | 342.2 | Scheme 1 |
| 18 | 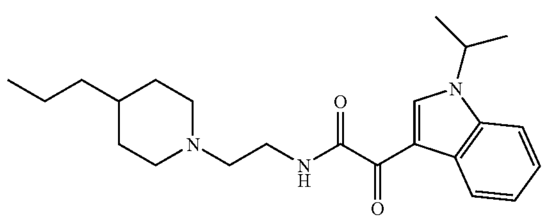 | 384.4 | 383.3 | Schemes 1 and 3 |
| 19 | 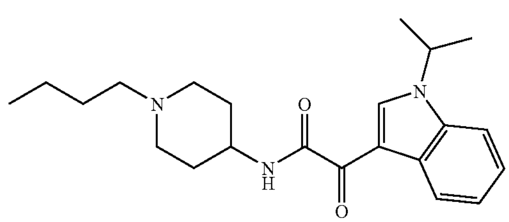 | 370.3 | 369.2 | Scheme 2 |
| 20 | 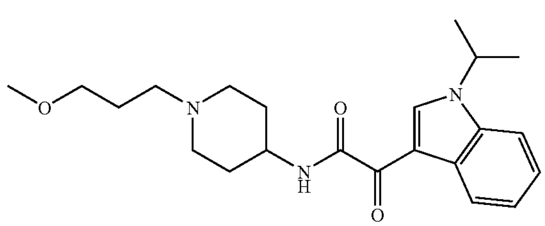 | 386.4 | 385.2 | Scheme 2 |

TABLE 1-continued

EXAMPLE COMPOUNDS

| Example No. | Structure | m/z | Calc MW | Synthetic Methods |
|---|---|---|---|---|
| 21 | 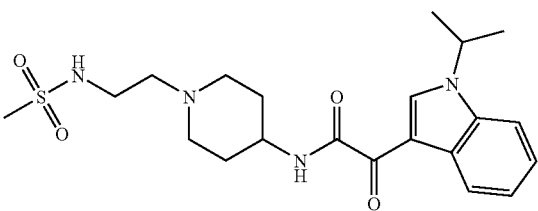 | 435.4 | 434.2 | Scheme 2 |
| 22 | 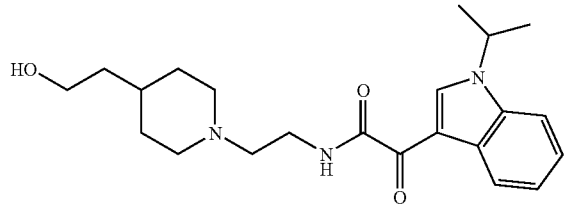 | 385.5 | 385.2 | Schemes 1 and 3 |
| 23 | 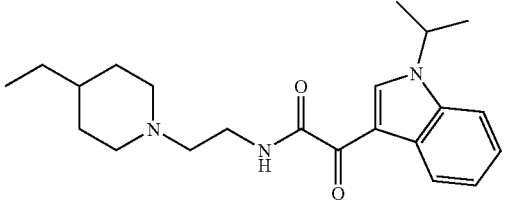 | 369.5 | 369.2 | Schemes 1 and 3 |
| 24 | 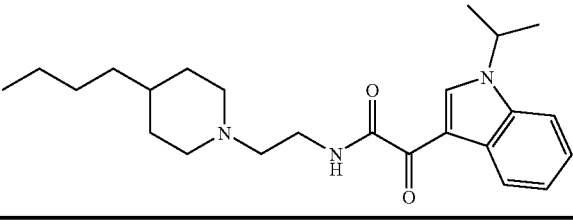 | 398.3 | 397.3 | Scheme 4 |

Example 25

Binding Affinity Assay

The binding affinity of compounds of the invention to the 5-HT$_4$ receptors were determined and are shown in table 2. The evaluation of the affinity of compounds for the human 5-HT4e receptor in transfected CHO cells was determined in a radioligand binding assay. Experimental protocol: Cell membrane homogenates (140 μg protein) were incubated for 60 mM at 37° C. with 0.3 nM [3H]GR 113808 in the absence or presence of the test compound in a buffer containing 50 mM Hepes/Tris (pH 7.4) and 1 μM pargyline. Nonspecific binding was determined in the presence of 100 μM 5-HT. Following incubation, the samples were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard). The results are expressed as a percent inhibition of the control radioligand specific binding at a certain concentration of the test compound. The test compound can also be assessed at several concentrations to obtain a competition curve from which its IC$_{50}$ and K$_i$ are calculated.

TABLE 2
| Example No. | Structure | KI (μM or % inhibition) |
|---|---|---|
| 1 | 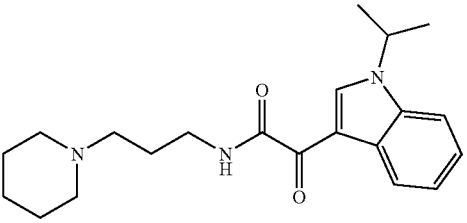 | 0.007 |
| 2 | 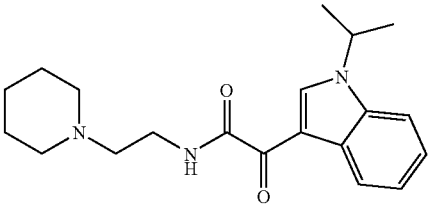 | 0.005 |
| 3 | 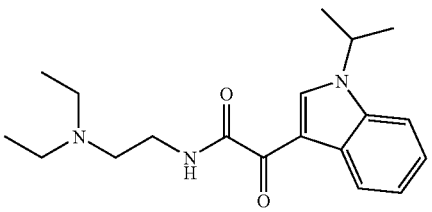 | 0.008 |
| 4 | 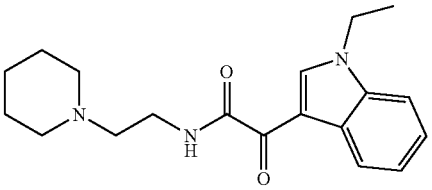 | 0.005 |
| 5 | 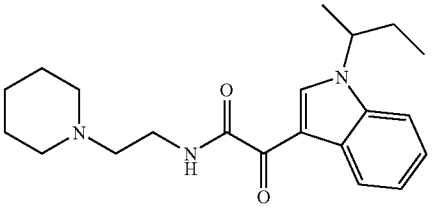 | 0.031 |
| 6 | 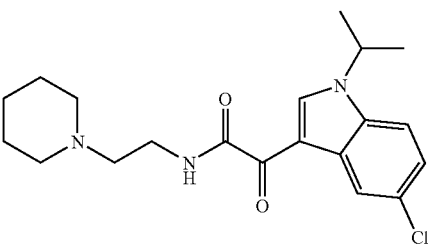 | 0.047 |

TABLE 2-continued

Assay Data

| Example No. | Structure | KI (μM or % inhibition) |
|---|---|---|
| 7 | 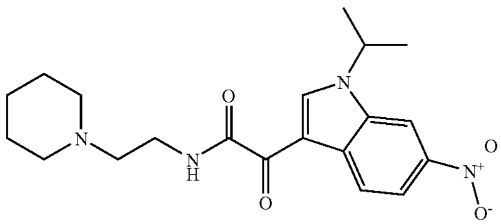 | 2.7 |
| 8 | 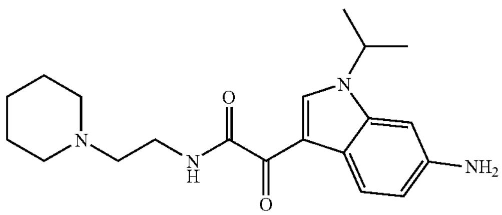 | 0.75 |
| 9 | 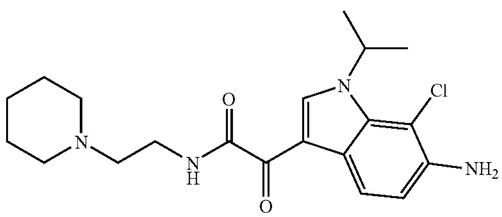 | 0.1 |
| 10 | 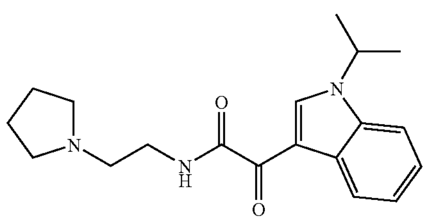 | 0.013 |
| 11 | 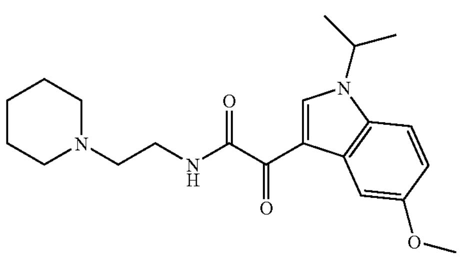 | 0.31 |
| 12 | 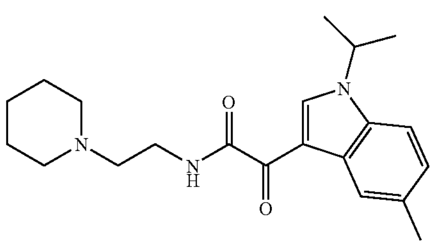 | 0.071 |

TABLE 2-continued

Assay Data

| Example No. | Structure | KI (μM or % inhibition) |
|---|---|---|
| 13 | 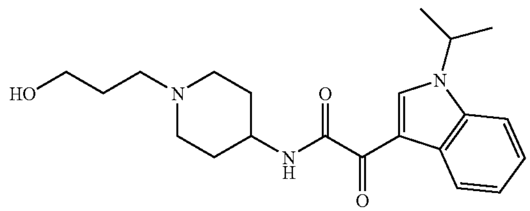 | 0.0024 |
| 14 | 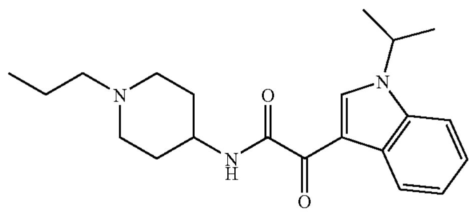 | 0.0027 |
| 15 | 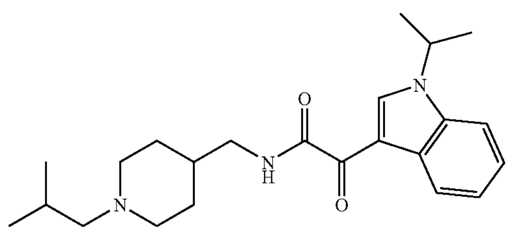 | 0.016 |
| 16 | 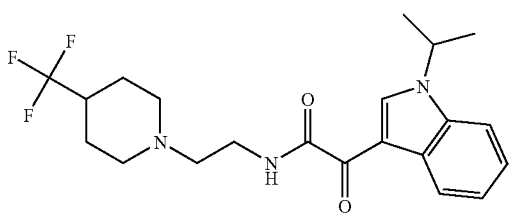 | 0.023 |
| 17 | 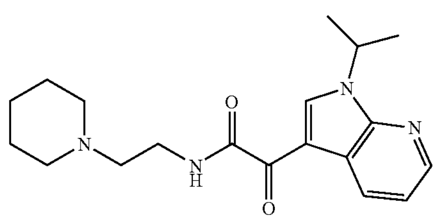 | 0.022 |
| 18 | 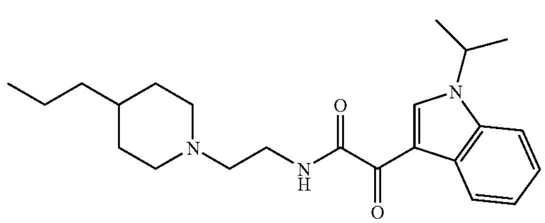 | 99% @ 0.3 uM<br>102% @ 3 uM |
| 19 | 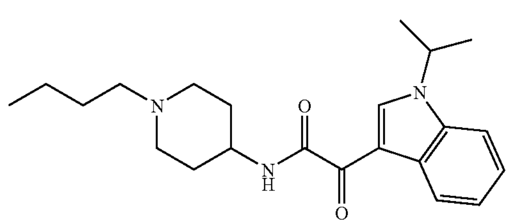 | 0.0025 |

TABLE 2-continued

Assay Data

| Example No. | Structure | KI (µM or % inhibition) |
|---|---|---|
| 20 | 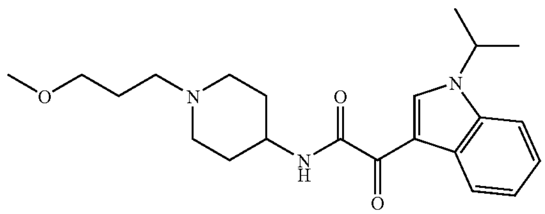 | 0.0069 |
| 21 | 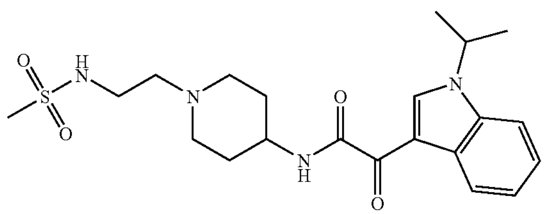 | 95% @ 0.3 uM<br>101% @ 3 uM |
| 22 | 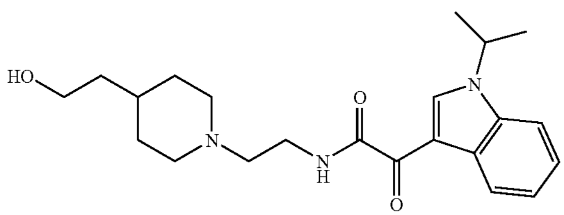 | 99% @ 0.3 uM<br>101% @ 3 uM |
| 23 | 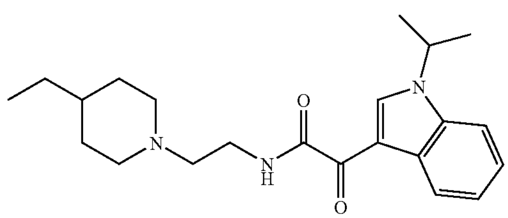 | 99% @ 0.3 uM<br>101% @ 3 uM |
| 24 | 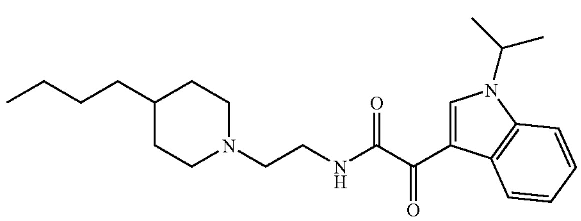 | 95% @ 0.3 uM<br>101% @ 3 uM |

All publications and patents mentioned herein, including those items listed below, are hereby incorporated by reference in their entirety as if each individual publication or patent was specifically and individually incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound of formula II:

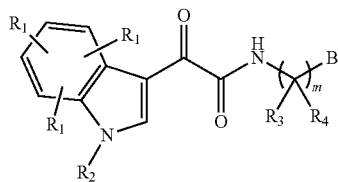

or pharmaceutically acceptable salts or N-oxides thereof, wherein $R_1$ is, independently for each occurrence, selected from halogen, hydroxyl, $C_1$-$C_6$ alkyl, $C_1$-$C_6$ haloalkyl, $C_3$-$C_6$ cycloalkyl, $C_1$-$C_6$ alkoxy, nitro, cyano, amino, sulfonyl, $C_1$-$C_6$ alkylsulfonyl, sulfamoyl, carbamoyl, carboxyl, N—$C_1$-$C_6$ alkylsulfamoyl, and N—$C_1$-$C_6$ alkylcarbamoyl;

B is selected from formulae IIA and IIB:

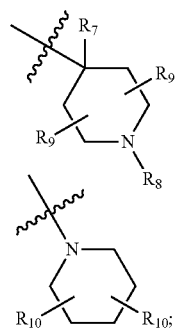

$R_2$ is selected from $C_1$-$C_6$ alkyl and $C_3$-$C_6$ cycloalkyl, wherein $R_2$ may be optionally substituted with one, two, or three substituents selected, independently for each occurrence, from halogen, alkoxy, nitro, cyano, amino, and carboxyl;

$R_3$ and $R_4$ are each independently selected from hydrogen, $C_1$-$C_6$ alkoxy, $C_1$-$C_6$ alkyl, aryl, $C_3$-$C_6$ cycloalkyl, halogen, heteroaryl, heterocyclyl, and hydroxyl, wherein $R_3$ or $R_4$, if not hydrogen, may be optionally substituted by one, two, or three substituents represented by $R_{10}$, or $R_3$ and $R_4$ are taken together with the carbon atom to which they are attached to form a four, five, or six membered heterocyclyl or $C_3$-$C_6$ cycloalkyl optionally substituted by one, two, or three substituents each represented by $R_{10}$;

$R_7$ is selected from $C_1$-$C_6$ alkoxy, $C_1$-$C_6$ alkyl, cyano, halogen, hydrogen, and hydroxyl;

$R_8$ is selected from hydrogen and alkyl optionally substituted by one, two, or three substituents each selected from halogen, hydroxyl, $C_1$-$C_6$ alkylsulfonyl, $C_1$-$C_6$ alkoxy, N—$C_1$-$C_6$ alkylamino, N,N-di$C_1$-$C_6$ alkylamino, cyano, carboxyl, sulfonamido, and $C_1$-$C_6$alkylsulfonamido;

$R_9$ is, independently for each occurrence, selected from hydrogen, halogen, hydroxyl, nitro, cyano, amino, sulfonyl, $C_1$-$C_6$alkylsulfonyl, sulfamoyl, sulfonamido, $C_1$-$C_6$ alkylsulfonamido, carbamoyl, carboxyl, N—$C_1$-$C_6$ alkylsulfamoyl, and N—$C_1$-$C_6$ alkylcarbamoyl, $C_1$-$C_6$ alkyl, $C_3$-$C_6$ cycloalkyl, $C_1$-$C_6$ alkylthio, and $C_1$-$C_6$ alkoxy, wherein the alkyl, cycloalkyl or alkoxy is optionally substituted by one, two, or three substituents independently selected from halogen, hydroxyl, carboxy, cyano, amido, nitro, and amino;

$R_{10}$ is, independently for each occurrence, selected from halogen, hydroxyl, nitro, cyano, amino, sulfonyl, $C_1$-$C_6$ alkylsulfonyl, sulfamoyl, sulfonamido, $C_1$-$C_6$ alkylsulfonamido, carbamoyl, carboxyl, N—$C_1$-$C_6$ alkylsulfamoyl, and N—$C_1$-$C_6$ alkylcarbamoyl, $C_1$-$C_6$ alkyl, $C_3$-$C_6$ cycloalkyl, $C_1$-$C_6$ alkylthio, and $C_1$-$C_6$ alkoxy, wherein the alkyl, cycloalkyl or alkoxy is optionally substituted by one, two, or three substituents independently selected from halogen, hydroxyl, carboxy, cyano, amido, nitro, and amino; and m is 0, 1, 2, 3, or 4.

2. A compound selected from:
2-(1-isopropyl-1H-indol-3-yl)-2-oxo-N-(3-(piperidin-1-yl)propyl)acetamide;
2-(1-isopropyl-1H-indol-3-yl)-2-oxo-N-(2-(piperidin-1-yl)ethyl)acetamide;
N-(2-(diethylamino)ethyl)-2-(1-isopropyl-1H-indol-3-yl)-2-oxoacetamide;
2-(1-ethyl-1H-indol-3-yl)-2-oxo-N-(2-(piperidin-1-yl)ethyl)acetamide;
2-(1-sec-butyl-1H-indol-3-yl)-2-oxo-N-(2-(piperidin-1-yl)ethyl)acetamide;
2-(5-chloro-1-isopropyl-1H-indol-3-yl)-2-oxo-N-(2-(piperidin-1-yl)ethyl)acetamide;
2-(1-isopropyl-6-nitro-1H-indol-3-yl)-2-oxo-N-(2-(piperidin-1-yl)ethyl)acetamide;
2-(6-amino-1-isopropyl-1H-indol-3-yl)-2-oxo-N-(2-(piperidin-1-yl)ethyl)acetamide;
2-(6-amino-7-chloro-1-isopropyl-1H-indol-3-yl)-2-oxo-N-(2-(piperidin-1-yl)ethyl)acetamide;
2-(1-isopropyl-1H-indol-3-yl)-2-oxo-N-(2-(pyrrolidin-1-yl)ethyl)acetamide;
2-(1-isopropyl-5-methoxy-1H-indol-3-yl)-2-oxo-N-(2-(piperidin-1-yl)ethyl)acetamide;
2-(1-isopropyl-5-methyl-1H-indol-3-yl)-2-oxo-N-(2-(piperidin-1-yl)ethyl)acetamide;
N-(1-(3-hydroxypropyl)piperidin-4-yl)-2-(1-isopropyl-1H-indol-3-yl)-2-oxoacetamide;
2-(1-isopropyl-1H-indol-3-yl)-2-oxo-N-(1-propylpiperidin-4-yl)acetamide;
N-((1-isobutylpiperidin-4-yl)methyl)-2-(1-isopropyl-1H-indol-3-yl)-2-oxoacetamide;
2-(1-isopropyl-1H-indol-3-yl)-2-oxo-N-(2(4-(trifluoromethyl)piperidin-1-yl)ethyl)acetamide;
N-(1-butylpiperidin-4-yl)-2-(1-isopropyl-1H-indol-3-yl)-2-oxoacetamide;
2-(1-isopropyl-1H-indol-3-yl)-N-(1-(3-methoxypropyl)piperidin-4-yl)-2-oxoacetamide;
2-(1-isopropyl-1H-pyrrolo[2,3-b]pyridin-3-yl)-2-oxo-N-(2-(piperidin-1-yl)ethyl)acetamide;
2-(1-isopropyl-1H-indol-3-yl)-N-(1-(2-(methylsulfonamido)ethyl)piperidin-4-yl)-2-oxoacetamide;
2-(1-isopropyl-1H-indol-3-yl)-2-oxo-N-(2-(4-propylpiperidin-1-yl)ethyl)acetamide;
N-(2-(4-(2-hydroxyethyl)piperidin-1-yl)ethyl)-2-(1-isopropyl-1H-indol-3-yl)-2-oxoacetamide;
N-(2-(4-ethylpiperidin-1-yl)ethyl)-2-(1-isopropyl-1H-indol-3-yl)-2-oxoacetamide; and
N-(2-(4-butylpiperidin-1-yl)ethyl)-2-(1-isopropyl-1H-indol-3-yl)-2-oxoacetamide,
or a pharmaceutically acceptable salt or N-oxide thereof.

3. A compound selected from:
2-(1-ethyl-1H-indol-3-yl)-2-oxo-N-(3-(piperidin-1-yl)propyl)acetamide;

N-(2-(ethyl(methyl)amino)ethyl)-2-(1-isopropyl-1H-indol-3-yl)-2-oxoacetamide;
2-(1-sec-butyl-1H-indol-3-yl)-2-oxo-N-(3-(piperidin-1-yl)propyl)acetamide;
2-(1-isobutyl-1H-indol-3-yl)-2-oxo-N-(3-(piperidin-1-yl)propyl)acetamide;
2-(1-isopropyl-1H-indol-3-yl)-2-oxo-N-(3-(pyrrolidin-1-yl)propyl)acetamide;
N-(3-(ethyl(methyl)amino)propyl)-2-(1-isopropyl-1H-indol-3-yl)-2-oxoacetamide;
2-(1-isobutyl-1H-indol-3-yl)-2-oxo-N-(2-(piperidin-1-yl)ethyl)acetamide;
2-(1-isopropyl-1H-indol-3-yl)-2-oxo-N-(2-(pyrrolidin-1-yl)ethyl)acetamide;
(R)-2-(1-sec-butyl-1H-indol-3-yl)-2-oxo-N-(3-(piperidin-1-yl)propyl)acetamide;
(S)-2-(1-sec-butyl-1H-indol-3-yl)-2-oxo-N-(3-(piperidin-1-yl)propyl)acetamide;
(S)-2-(1-sec-butyl-1H-indol-3-yl)-2-oxo-N-(2-(piperidin-1-yl)ethyl)acetamide;
(R)-2-(1-sec-butyl-1H-indol-3-yl)-2-oxo-N-(2-(piperidin-1-yl)ethyl)acetamide;
2-(4-hydroxy-1-isopropyl-1H-indol-3-yl)-2-oxo-N-(3-(piperidin-1-yl)propyl)acetamide;
2-(4-hydroxy-1-isopropyl-1H-indol-3-yl)-2-oxo-N-(2-(piperidin-1-yl)ethyl)acetamide;
2-(1-ethyl-4-hydroxy-1H-indol-3-yl)-2-oxo-N-(2-(piperidin-1-yl)ethyl)acetamide;
2-(6-amino-1-isopropyl-1H-indol-3-yl)-2-oxo-N-(3-(piperidin-1-yl)propyl)acetamide;
2-(5-amino-6-chloro-1-isopropyl-1H-indol-3-yl)-2-oxo-N-(3-(piperidin-1-yl)propyl)acetamide;
2-(6-amino-5-chloro-1-isopropyl-1H-indol-3-yl)-2-oxo-N-(2-(piperidin-1-yl)ethyl)acetamide;
2-(5-amino-6-chloro-1-isopropyl-1H-indol-3-yl)-2-oxo-N-(2-(piperidin-1-yl)ethyl)acetamide;
2-(1-isopropyl-1H-indol-3-yl)-N-(2-(4-methylpiperidin-1-yl)ethyl)-2-oxoacetamide;
2-(1-isopropyl-1H-pyrrolo[2,3-c]pyridin-3-yl)-2-oxo-N-(2-(piperidin-1-yl)ethyl)acetamide;
2-(1-isopropyl-1H-pyrrolo[3,2-b]pyridin-3-yl)-2-oxo-N-(2-(piperidin-1-yl)ethyl)acetamide;
2-(1-isopropyl-1H-pyrrolo[3,2-c]pyridin-3-yl)-2-oxo-N-(2-(piperidin-1-yl)ethyl)acetamide;
2-(4-isopropyl-4H-thieno[3,2-b]pyrrol-6-yl)-2-oxo-N-(2-(piperidin-1-yl)ethyl)acetamide;
2-(1-isopropyl-2-methyl-1H-indol-3-yl)-2-oxo-N-(2-(piperidin-1-yl)ethyl)acetamide;
2-(2-ethyl-1-isopropyl-1H-indol-3-yl)-2-oxo-N-(2-(piperidin-1-yl)ethyl)acetamide;
2-(1-isopropyl-1H-indol-3-yl)-N-(1-morpholinopropan-2-yl)-2-oxoacetamide;
2-(1-isopropyl-1H-indol-3-yl)-2-oxo-N-((1-propylpyrrolidin-3-yl)methyl)acetamide;
N-((1-dimethylamino)cyclopentyl)methyl)-2-(1-isopropyl-1H-indol-3-yl)-2-oxoacetamide;
N-(1-ethylpiperidin-3-yl)-2-(1-isopropyl-1H-indol-3-yl)-2-oxoacetamide;
N-((1-ethylpyrrolidin-2-yl)methyl)-2-(1-isopropyl-1H-indol-3-yl)-2-oxoacetamide;
N-((4-hydroxy-1-methylpiperidin-4-yl)methyl)-2-(1-isopropyl-1H-indol-3-yl)-2-oxoacetamide;
N-(3-(dimethylamino)cyclopentyl)-2-(1-isopropyl-1H-indol-3-yl)-2-oxoacetamide;
N-(3-(dimethylamino)cyclohexyl)-2-(1-isopropyl-1H-indol-3-yl)-2-oxoacetamide;
N-(2-(3-fluoropyrrolidin-1-yl)ethyl)-2-(1-isopropyl-1H-indol-3-yl)-2-oxoacetamide;
N-(2-((2-fluoroethyl)(methyl)amino)ethyl)-2-(1-isopropyl-1H-indol-3-yl)-2-oxoacetamide;
N-(2-(4-fluoropiperidin-1-yl)ethyl)-2-(1-isopropyl-1H-indol-3-yl)-2-oxoacetamide;
N-(2-(3-hydroxypyrrolidin-1-yl)ethyl)-2-(1-isopropyl-1H-indol-3-yl)-2-oxoacetamide;
2-(1-isopropyl-1H-indol-3-yl)-N-(2-(3-(methylsulfonyl)pyrrolidin-1-yl)ethyl)-2-oxoacetamide;
N-(2-(4-ethoxypiperidin-1-yl)ethyl)-2-(1-isopropyl-1H-indol-3-yl)-2-oxoacetamide;
N-(2-(4-(dimethylamino)piperidin-1-yl)ethyl)-2-(1-isopropyl-1H-indol-3-yl)-2-oxoacetamide;
N-(2-(4-ethylpiperazin-1-yl)ethyl)-2-(1-isopropyl-1H-indol-3-yl)-2-oxoacetamide;
2-(1-isopropyl-1H-indazol-3-yl)-2-oxo-N-(2-(piperidin-1-yl)ethyl)acetamide;
2-(1-(2-hydroxyethyl)-1H-indol-3-yl)-2-oxo-N-(2-(piperidin-1-yl)ethyl)acetamide;
(R)—N-(2-(4-(2-hydroxy-3-(N-methylmethylsulfonamido)propyl)piperidin-1-yl)ethyl)-2-(1-isopropyl-1H-indol-3-yl)-2-oxoacetamide;
2-(1-isopropyl-1H-indol-3-yl)-N-(2-(4-(3-(methylsulfonyl)propyl)piperidin-1-yl)ethyl)-2-oxoacetamide;
N-(3-(diethylamino)propyl)-2-(1-isopropyl-1H-indol-3-yl)-2-oxoacetamide;
N-(4-(diethylamino)cyclohexyl)-2-(1-isopropyl-1H-indol-3-yl)-2-oxoacetamide;
N-(1-ethylpiperidin-4-yl)-2-(1-isopropyl-1H-indol-3-yl)-2-oxoacetamide;
2-(1-isopropyl-1H-indol-3-yl)-N-(3-(4-methylpiperidin-1-yl)propyl)-2-oxoacetamide;
N-(3-(4-ethylpiperidin-1-yl)propyl)-2-(1-isopropyl-1H-indol-3-yl)-2-oxoacetamide;
2-(1-isopropyl-1H-indol-3-yl)-2-oxo-N-(3-(4-propylpiperidin-1-yl)propyl)acetamide;
2-(1-isopropyl-1H-indol-3-yl)-2-oxo-N-((1-propylpiperidin-4-yl)methyl)acetamide;
N-((1-butylpiperidin-4-yl)methyl)-2-(1-isopropyl-1H-indol-3-yl)-2-oxoacetamide;
N-((4-chloro-1-methylpiperidin-4-yl)methyl)-2-(1-isopropyl-1H-indol-3-yl)-2-oxoacetamide;
N-((1,4-dimethylpiperidin-4-yl)methyl)-2-(1-isopropyl-1H-indol-3-yl)-2-oxoacetamide;
N-(2-(4-(dimethylamino)cyclohexyl)ethyl)-2-(1-isopropyl-1H-indol-3-yl)-2-oxoacetamide;
N-(2-(4-(ethylamino)cyclohexyl)ethyl)-2-(1-isopropyl-1H-indol-3-yl)-2-oxoacetamide;
N-((4-(dimethylamino)cyclohexyl)methyl)-2-(1-isopropyl-1H-indol-3-yl)-2-oxoacetamide;
N-((4-(diethylamino)cyclohexyl)methyl)-2-(1-isopropyl-1H-indol-3-yl)-2-oxoacetamide;
2-(1-isopropyl-1H-indol-3-yl)-N-(6-isopropylpiperidin-3-yl)-2-oxoacetamide;
N-(6-butylpiperidin-3-yl)-2-(1-isopropyl-1H-indol-3-yl)-2-oxoacetamide;
N-(6-(3-hydroxypropyl)piperidin-3-yl)-2-(1-isopropyl-1H-indol-3-yl)-2-oxoacetamide;
2-(1-(1-chloroethyl)-1H-indol-3-yl)-N-(2-(diethylamino)ethyl)-2-oxoacetamide;
N-(2-(diethylamino)ethyl)-2-oxo-2-(1-(2-oxopropyl)-1H-indol-3-yl)acetamide;
2-(1-(1-cyanoethyl)-1H-indol-3-yl)-N-(2-(diethylamino)ethyl)-2-oxoacetamide;
N-(2-(4-(3-hydroxypropyl)piperidin-1-yl)ethyl)-2-(1-isopropyl-1H-indol-3-yl)-2-oxoacetamide;

N-((1-(3-hydroxypropyl)piperidin-4-yl)methyl)-2-(1-isopropyl-1H-indol-3-yl)-2-oxoacetamide;
N-(1-(3-hydroxybutyl)piperidin-4-yl)-2-(1-isopropyl-1H-indol-3-yl)-2-oxoacetamide;
N-((1-ethyl-4-hydroxypiperidin-4-yl)methyl)-2-(1-isopropyl-1H-indol-3-yl)-2-oxoacetamide;
N-((4-hydroxy-1-propylpiperidin-4-yl)methyl)-2-(1-isopropyl-1H-indol-3-yl)-2-oxoacetamide;
N-((1-butyl-4-hydroxypiperidin-4-yl)methyl)-2-(1-isopropyl-1H-indol-3-yl)-2-oxoacetamide;
N,N-diethyl-4-(4-(2-(1-isopropyl-1H-indol-3-yl)-2-oxoacetamido)piperidin-1-yl)butanamide;
2-(1-isopropyl-1H-indol-3-yl)-N-(3-morpholinopropyl)-2-oxoacetamide;
2-(1-isopropyl-1H-indol-3-yl)-2-oxo-N-(4-(piperidin-1-yl)butyl)acetamide;
2-(1-isopropyl-1H-indol-3-yl)-2-oxo-N-(1-pentylpiperidin-4-yl)acetamide;
N-(1-hexylpiperidin-4-yl)-2-(1-isopropyl-1H-indol-3-yl)-2-oxoacetamide;
3-(4-(2-(1-isopropyl-1H-indol-3-yl)-2-oxoacetamido)piperidin-1-yl)-N,N-dimethylpropanamide;
2-(3-(2-oxo-2-(2-(piperidin-1-yl)ethylamino)acetyl)-1H-indol-1-yl)acetic acid;
3-(3-(2-oxo-2-(2-(piperidin-1-yl)ethylamino)acetyl)-1H-indol-1-yl)propanoic acid;
2-(3-(2-oxo-2-(2-(piperidin-1-yl)ethylamino)acetyl)-1H-indol-1-yl)propanoic acid;
1-(2-(2-(1-isopropyl-1H-indol-3-yl)-2-oxoacetamido)ethyl)piperidine-4-carboxylic acid;
N-(3-(4-(2-hydroxyethyl)piperidin-1-yl)propyl)-2-(1-isopropyl-1H-indol-3-yl)-2-oxoacetamide;
2-(1-isopropyl-1H-indol-3-yl)-N-(1-(2-methoxyethyl)piperidin-4-yl)-2-oxoacetamide;
2-(1-isopropyl-1H-indol-3-yl)-N-(2-(4-(methoxymethyl)piperidin-1-yl)ethyl)-2-oxoacetamide;
N-(2-(4-(2-hydroxypropyl)piperidin-1-yl)ethyl)-2-(1-isopropyl-1H-indol-3-yl)-2-oxoacetamide;
2-(5-fluoro-1-isopropyl-1H-indol-3-yl)-2-oxo-N-(2-(piperidin-1-yl)ethyl)acetamide;
2-(5-fluoro-1-methyl-1H-indol-3-yl)-2-oxo-N-(2-(piperidin-1-yl)ethyl)acetamide;
2-(1-methyl-1H-indol-3-yl)-2-oxo-N-(2-(piperidin-1-yl)ethyl)acetamide;
2-(1-isopropyl-1H-indol-3-yl)-N-(1-(2-(methylthio)ethyl)piperidin-4-yl)-2-oxoacetamide; and
2-(1-isopropyl-1H-indol-3-yl)-2-oxo-N-(1-(4,4,4-trifluorobutyl)piperidin-4-yl)acetamide, or a pharmaceutically acceptable salt or N-oxide thereof.

4. A pharmaceutical composition comprising a compound, or a pharmaceutically acceptable salt or N-oxide thereof, according to claim 1 and a pharmaceutically acceptable carrier.

\* \* \* \* \*